(12) United States Patent
Roos et al.

(10) Patent No.: US 11,857,582 B2
(45) Date of Patent: Jan. 2, 2024

(54) THERAPEUTIC MICROVESICLES OF PROBIOTIC BACTERIA

(71) Applicant: BioGaia AB, Stockholm (SE)

(72) Inventors: Stefan Roos, Uppsala (SE); Wolfgang Kunze, Hamilton (CA); John Bienenstock, Toronto (CA)

(73) Assignee: BioGaia AB, Stockholm (SE)

( * ) Notice: Subject to any disclaimer, the term of this patent is extended or adjusted under 35 U.S.C. 154(b) by 338 days.

(21) Appl. No.: 17/045,315

(22) PCT Filed: Apr. 17, 2020

(86) PCT No.: PCT/SE2020/050397
§ 371 (c)(1),
(2) Date: Oct. 5, 2020

(87) PCT Pub. No.: WO2020/214083
PCT Pub. Date: Oct. 22, 2020

(65) Prior Publication Data
US 2021/0154245 A1    May 27, 2021

(30) Foreign Application Priority Data

Apr. 17, 2019 (SE) .................. 1950483-6
Oct. 25, 2019 (SE) .................. 1951222-7

(51) Int. Cl.
*A61K 35/747* (2015.01)
*A61P 1/00* (2006.01)
*A61K 35/745* (2015.01)

(52) U.S. Cl.
CPC .......... *A61K 35/747* (2013.01); *A61K 35/745* (2013.01); *A61P 1/00* (2018.01)

(58) Field of Classification Search
CPC .......... C12N 1/20; C12N 1/04; A61K 35/745; A61K 35/747; A61K 2300/00; A61P 1/00; A61P 1/14; A61P 19/10; C12R 2001/01
See application file for complete search history.

(56) References Cited

U.S. PATENT DOCUMENTS

2013/0195765 A1    8/2013    Gho et al.

FOREIGN PATENT DOCUMENTS

| WO | 2018202657 A1 | 11/2018 | |
| WO | WO-2018202657 A1 * | 11/2018 | ............. A61K 35/74 |
| WO | 2020214083 A1 | 10/2020 | |

OTHER PUBLICATIONS

International Depository Authority DSM 17938 dated Feb. 6, 2006; Viability Statement DSM 17938 dated Feb. 6, 2006; 2 pages.
International Depository Authority DSM 32947 dated Nov. 19, 2018; Viability Statement DSM 32947 dated Nov. 19, 2018; 4 pages.

(Continued)

*Primary Examiner* — Jana A Hines
(74) *Attorney, Agent, or Firm* — McNeill Baur PLLC

(57) ABSTRACT

A method to provide therapeutic microvesicles from probiotic bacteria comprises exposing the bacteria to an inducing treatment during culturing to induce production of therapeutic microvesicles by the bacteria. The therapeutic microvesicles may be used in treatment of, for instance, colic, an infant or childhood gastrointestinal disorder or disease, a gastrointestinal pain disorder, a bone loss disease and/or a periodontal disease.

13 Claims, 20 Drawing Sheets

(56) References Cited

OTHER PUBLICATIONS

International Depository Authority DSM 32948 dated Nov. 19, 2018; Viability Statement DSM 32948 dated Nov. 19, 2018; 4 pages.

Britton et al: "Probiotic L. reuteri Treatment Prevents Bone Loss in a Menopausal Ovariectomized Mouse Model", Journal of Cellular Physiology, vol. 229, No. 11, Nov. 2014, pp. 1822-1830.

Al-Nedawi et al: "Gut commensal microvesicles reproduce parent bacterial signals to host immune and enteric hervous systems", The FASEB Journal, vol. 29, No. 2, 2015, pp. 684-695.

International Depository Authority DSM 32846 dated Jul. 4, 2018; Viability Statement DSM 32846 dated Jul. 4, 2018; 4 pages.

International Search Report and Written Opinion issued for PCT/SE2020/050397, dated Jul. 7, 2020; 12 pages.

Rubio et al: "Lactobacillus casei BL23 Produces Microvesicles Carrying Proteins That Have Been Associated with Its Probiotic Effect", Frontiers in Microbiology, vol. 8, Sep. 2017.

Szajewska et al.: "Lactobacillus reuteri DSM 17938 for the Management of Infantile Colic in Breastfed Infants: A Randomized, Double-Blind, Placebo-Controlled Trial", The Journal of Pediatrics, vol. 162, No. 2, 2013, pp. 257-262.

Szkaradkiewicz et al: "Effect of Oral Administration Involving a Probiotic Strain of Lactobacillus reuterion Pro-Inflammatory Cytokine Response in Patients with Chronic Periodontitis", Archivum Immunologiae Et Therapiae Experimentalis, Birkhaeuser Verlag AG, CH, vol. 62, No. 6, Feb. 9, 2014, pp. 495-500.

Pang et al., "Extracellular membrane vesicles from Limosilactobacillus reuteri strengthen the intestinal epithelial integrity, modulate cytokine responses and antagonize activation of TRPV1", Frontiers in Microbiology: pp. 1-17 (2022).

Rosander et al., "Removal of Antibiotic Resistance Gene-Carrying Plasmids from Lactobacillus reuteri ATCC 55730 and Characterization of the Resulting Daughter Strain, L. reuteri DSM 17938", Applied and Environ. Microbiology, 74 (19), pp. 6032-6040 (2008).

\* cited by examiner

| Jejunum | DSM | CM | Broth | µV | CM - µV |
|---|---|---|---|---|---|
| Velocity | ↓↓ | ↓↓ | ↓ | ↓↓ | · |
| Frequency | ↓↓ | · | ↓ | ↓↓ | · |
| Peak Amplitude | ↓ | ↓ | · | ↓ | · |

| Colon | DSM | CM | Broth | µV | CM - µV |
|---|---|---|---|---|---|
| Velocity | ↑↑ | ↑↑ | · | ↑ | · |
| Frequency | ↑↑ | ↑↑ | · | ↑ | · |
| Peak Amplitude | ↑ | · | · | · | · |

Fig. 8

THERAPEUTIC MICROVESICLES OF PROBIOTIC BACTERIA

This application is a national phase entry pursuant to 35 U.S.C. § 371 of International Application No. PCT/SE2020/050397, filed Apr. 17, 2020, which claims the benefit of SE Application No. 1950483-6, filed Apr. 17, 2019, and SE Application No. 1951222-7, filed Oct. 25, 2019, each of which is incorporated by reference herein in its entirety.

TECHNICAL FIELD

The present invention generally relates to therapeutic microvesicles of probiotic bacteria and uses thereof.

BACKGROUND

The Food and Agricultural Organization of the United Nations has defined probiotics as "live microorganisms which, when administered in adequate amounts, confer a health benefit on the host". Probiotics influence immune functions of the host, either via modulation of the microbiota composition, via metabolic activity, or even through a direct interaction with the immune system underlying the gut mucosa. Over 60% of the immune cells are located in the gut mucosa, and the sampling information of the microbiota structure and composition is translated into local and systemic effects through circulating immune cells. Following probiotic interactions, immune mechanisms may be activated as reflected by the release of immune mediators, such as cytokines, production of antibodies and activation of lymphocytes as well as other immune cells. These activated cells, cytokines and/or compounds released by the probiotics will exert immune modulatory functions at different locations within the body through the blood circulation. Probiotics can also prevent or inhibit the proliferation of pathogens and suppress production of virulence factors by pathogens.

Several different bacterial strains are currently used as probiotics, including lactic acid producing bacteria, such as selected strains of *Lactobacillus* and *Bifidobacterium*. The effectiveness of probiotic bacteria is strain-specific, and each strain may contribute to host health through different mechanisms.

Numerous varieties of probiotic supplements exist but the beneficial health effect varies between bacterial strains and little is still known about ways of controlling and regulating the specific probiotic or biological effect. Each bacterial strain has distinct mechanisms by which specific effects are mediated to improve health and to relieve symptoms of, for instance, gastrointestinal disturbance, including diarrhea and constipation, inflammatory bowel disease (IBD), irritable bowel syndrome (IBS) and infant colic. Infant colic is a condition that can be extremely stressful for the families affected and significantly impair the quality of life. In addition, infant colic could potentially have long-term consequences for the infants later in life. The well-studied probiotic bacterial strain *Lactobacillus reuteri* DSM 17938 has been shown to significantly reduce crying-time in colicky infants. However, the time to onset of this effect is not immediate, and it may take from one to three weeks before the infant benefits from the treatment.

There is, thus, a great need for faster acting interventions, as well as even more efficient ones to, for instance, reduce the period of discomfort and crying for colicky children.

SUMMARY OF THE INVENTION

It is a general objective of the invention herein to provide therapeutic microvesicles from probiotic bacteria.

This and other objectives are met by the embodiments as disclosed herein.

The present invention is defined in the independent claims. Further embodiments of the invention are defined in the dependent claims.

An aspect of the embodiments relates to a method of producing therapeutic microvesicles. The method comprises culturing bacteria of a probiotic bacterial strain in a culture medium. The probiotic bacterial strain is selected from the group consisting of a *Lactobacillus* strain, a *Bifidobacterium* strain and a combination thereof. The method also comprises exposing the bacteria to an inducing biotic treatment during culturing to induce production of therapeutic microvesicles by the bacteria. The inducing biotic treatment is selected from the group consisting of co-culturing the bacteria with bacteria of another bacterial strain, culturing the bacteria in presence of a conditioned medium from bacteria of another bacterial strain and a combination thereof. The another bacterial strain is a *Bifidobacterium* strain and the another bacterial strain is different from the probiotic bacterial strain.

Other aspects of the embodiments relate to a probiotic composition comprising bacteria of a probiotic bacterial strain and therapeutic microvesicles produced by the probiotic bacterial strain or by another probiotic bacterial strain for use in treatment of colic and/or for use in treatment of a disease selected from the group consisting of an infant or childhood gastrointestinal disorder or disease, a gastrointestinal pain disorder, a bone loss disease a periodontal disease, and a combination thereof. The probiotic bacterial strain and the another probiotic bacterial strain are selected from the group consisting of a *Lactobacillus* strain, a *Bifidobacterium* strain, and a combination thereof.

Further aspects of the embodiments relate to a probiotic composition for use in treatment of colic and/or for use in treatment of a disease selected from the group consisting of an infant or childhood gastrointestinal disorder or disease, a gastrointestinal pain disorder, a bone loss disease a periodontal disease, and a combination thereof. The probiotic composition comprises a fast-acting component in the form of therapeutic microvesicles from bacteria of a probiotic bacterial strain. The probiotic bacterial strain is selected from the group consisting of a *Lactobacillus* strain, a *Bifidobacterium* strain, and a combination thereof. The probiotic composition also comprises a slow-acting component in the form of bacteria of the probiotic bacterial strain or of another probiotic bacterial strain. The another probiotic bacterial strain is selected from the group consisting of a *Lactobacillus* strain, a *Bifidobacterium* strain, and a combination thereof. The fast-acting component and the slow-acting component together produce a prolonged therapeutic effect when administered to a subject.

Yet other aspects of the embodiments relates to therapeutic microvesicles isolated from bacteria of a probiotic bacterial strain for use in treatment of colic and/or for use in treatment of a disease selected from the group consisting of an infant or childhood gastrointestinal disorder or disease, a gastrointestinal pain disorder, a bone loss disease a periodontal disease, and a combination thereof. The probiotic bacterial strain is selected from the group consisting of a *Lactobacillus* strain, a *Bifidobacterium* strain, and a combination thereof.

Another aspect of the embodiments relates to a bacterial strain, wherein the bacterial strain is *Bifidobacterium longum* DSM 32947 or *Bifidobacterium longum* DSM 32948.

A further aspect of the embodiments relates to a probiotic composition comprising bacteria of a *Lactobacillus* strain, preferably a *L. reuteri* strain, and more preferably a *L. reuteri* strain selected from the group consisting of *L. reuteri* DSM 17938, *L. reuteri* DSM 32846 and a combination thereof. The composition also comprises bacteria of a *Bifidobacterium longum* strain selected the group consisting of *B. longum* DSM 32947, *B. longum* DSM 32948 and a combination thereof, or a conditioned medium from the *B. longum* strain.

The therapeutic microvesicles, produced by probiotic bacteria, were able to recapitulate the beneficial effects of probiotic bacteria as shown herein. Furthermore, therapeutic microvesicles were in fact more efficient than the probiotic bacteria which produce them, as demonstrated by their faster onset of specific beneficial effects, as shown in the examples.

BRIEF DESCRIPTION OF THE DRAWINGS

The embodiments, together with further objects and advantages thereof, may best be understood by making reference to the following description taken together with the accompanying drawings, in which:

FIG. 3 illustrates the effects of adding DSM (FIG. 3A), CM (FIG. 3B), broth (FIG. 3C), μV (FIG. 3D) or CM-μV (FIG. 3E) on PCC frequency for mouse jejunal segments, in vitro.

FIG. 4 illustrates the effects of adding DSM (FIG. 4A), CM (FIG. 4B), broth (FIG. 4C), μV (FIG. 4D) or CM-μV (FIG. 4E) on PCC peak amplitude for mouse jejunal segments, in vitro.

FIG. 5 illustrates the effects of adding DSM (FIG. 5A), CM (FIG. 5B), broth (FIG. 5C), μV (FIG. 5D) or CM-μV (FIG. 5E) on PCC velocity for mouse colon segments, in vitro.

FIG. 6 illustrates the effects of adding DSM (FIG. 6A), CM (FIG. 6B), broth (FIG. 6C), μV (FIG. 6D) or CM-μV (FIG. 5E) on PCC frequency for mouse colon segments, in vitro.

FIG. 7 illustrates the effects of adding DSM (FIG. 7A), CM (FIG. 7B), broth (FIG. 7C), μV (FIG. 7D) or CM-μV (FIG. 7E) on PCC peak amplitude for mouse colon segments, in vitro.

FIG. 8 illustrates a summary of the results presented in FIGS. 2 to 7 on jejunum and colon velocity, frequency and peak amplitude.

(FIG. 11A) PBMC were cultured for 48 h in the presence of *L. reuteri* (L.r)-MVs at 500:1, 100:1, and 20:1 (MV:cell) ratio followed by quantification of secreted levels of IL-6, IL-10, IL-17A and IFN-γ (n=8). (FIG. 11B) PBMC were stimulated with *Staphylococcus aureus* (S.a)-CFS (2.5%) in the presence of L.r-MVs at 500:1, 100:1 and 20:1 (MV:cell) ratio followed by quantification of secreted levels of IFN-γ and IL-17A. Shown are relative values normalized *S. aureus*-CFS alone, (n=8). Boxes cover data between the 25th and the 75th percentile with medians as the central line and error bars showing min-to-max. Bar plots show median with interquartile range.

The figure also illustrate the protective effect of *L. reuteri* DSM 32846 derived MVs against ETEC damage to the monolayer in a FITC-dextran flux experiment.

Figure 22:
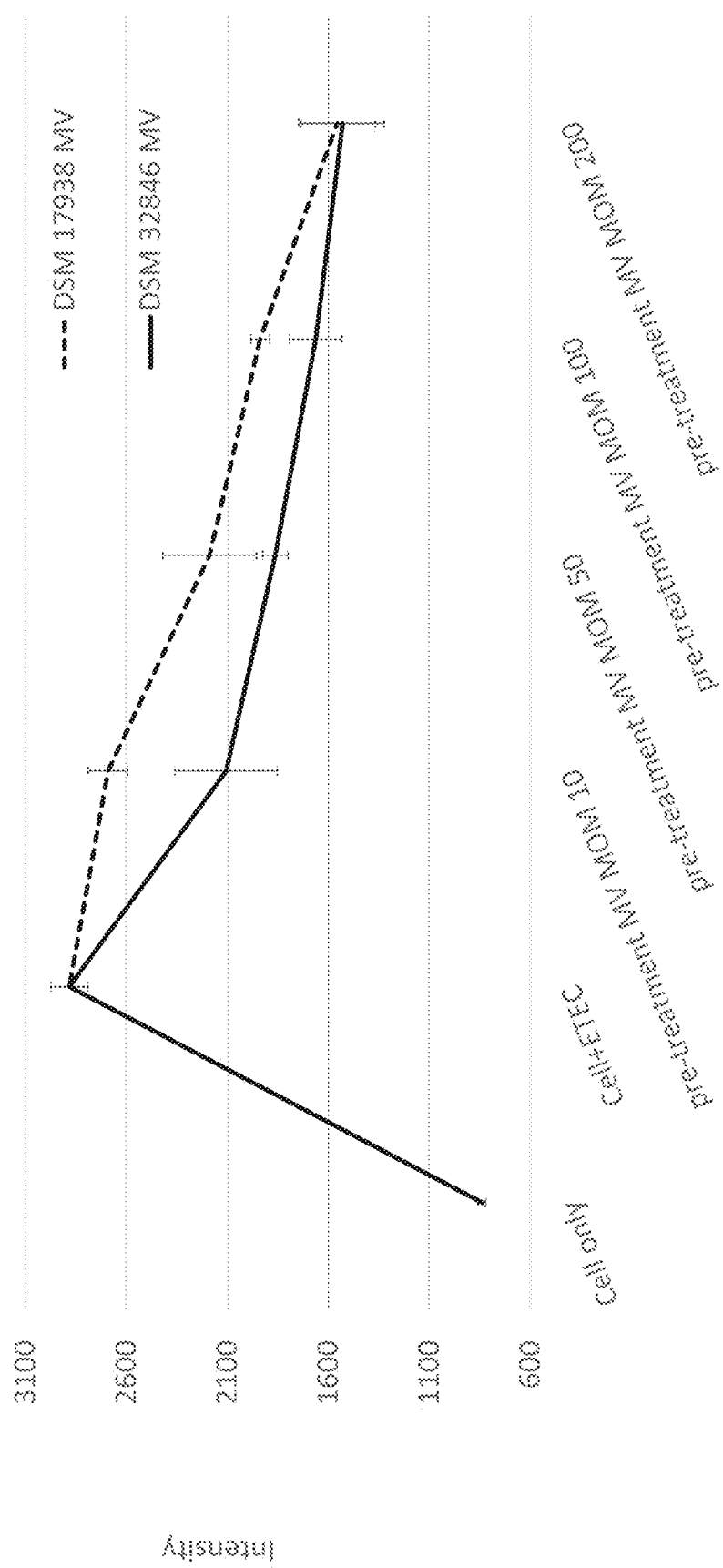

FIG. 22 illustrates a comparison between the protective effect of *L. reuteri* DSM 32846 derived MVs in the FITC-dextran flux experiment and the effect obtained with *L. reuteri* DSM 17938 derived MVs. Pre-treatment of the epithelial cell monolayers with *L. reuteri* DSM 32846 derived MVs decreased the leakage of FITC-dextran more efficiently, specifically at lower concentrations of MVs, compared to *L. reuteri* DSM 17938 derived MVs.

DETAILED DESCRIPTION

The present invention generally relates to therapeutic microvesicles from probiotic bacteria and uses thereof.

Definitions

Microvesicles (MVs, μV), also referred to as, for instance, membrane vesicles, outer membrane vesicles, extracellular vesicles in the art, are a demonstrated form of communication used by bacteria and eukaryotic cells. The release of bioactive MVs from the cell surface is conserved across microbial life, in bacteria, archaea, fungi, and parasites, and MV production has been demonstrated both in vitro and in vivo, implicating the influence of these surface organelles in microbial physiology and pathogenesis through their delivery of important signaling molecules, enzymes and toxins. Bacterial MVs are regularly produced and shed by both Gram-positive and Gram-negative bacteria, and proteomic experiments have shown that the contents of such MVs may be distinct from the content of the parent bacteria. The MVs may comprise lipid molecules, RNA molecules, DNA molecules, and/or protein. Furthermore, the MVs may also contain surface components of the parent bacteria.

The MVs produced by probiotic bacteria as disclosed herein are denoted therapeutic MVs herein to indicate that the MVs have a therapeutic effect. This therapeutic effect of the MVs could be the same or at least similar to the probiotic effect of the probiotic bacteria producing the MVs, when administered a subject. Accordingly, the MVs will exert a therapeutic effect in the subject, which will inhibit, treat or prevent, including delaying onset of, a medical condition, disease or disorder in the subject as is further described herein.

A culture medium or growth medium is the starting medium, in which bacteria will be cultured.

A conditioned medium is a culture or growth medium, in which bacteria have been cultured. Such a conditioned medium thereby comprises any compounds or agents, including MVs, released by the bacteria into the culture medium. The bacteria have been removed from the culture medium and are therefore not part of the conditioned medium. A conditioned medium can be obtained, for instance, by centrifugation, sedimentation and/or precipitation of the bacterial cell culture to obtain the conditioned medium as a supernatant.

A cell slurry is the mixture of cultured bacteria and culture medium including any compounds or agents, such as MVs, released by the bacteria into the culture medium, i.e., the conditioned medium. A cell slurry is the end result from fermentation.

The probiotic bacterial strain is preferably a strain of probiotic lactic acid producing bacteria, sometimes also referred to as lactic acid bacteria. Lactic acid producing bacteria are a group of Gram-positive, low % GC content of genome, acid-tolerant, generally non-sporulating, non-respiring, either rod- or cocci-shaped bacteria that share common metabolic and physiological characteristics. These bacteria produce lactic acid as the major metabolic end product of carbohydrate fermentation. Genera that comprise the lactic acid producing bacteria include *Lactobacillus, Leuconostoc, Pediococcus, Lactococcus*, and *Streptococcus*. *Bifidobacterium* is not included in the traditional lactic acid bacteria due to its genetic unrelatedness, but the bacterium has features that overlaps with lactic acid bacteria, and it has a metabolism that produces lactic acid as a primary end-product of fermentation, although it produces much less lactic acid than *Lactobacillus*. Bifidobacteria are strictly anaerobic and are normally found in high abundance in the large intestine.

MVs produced by probiotic bacteria are important by constituting a communication means between the probiotic bacteria and surrounding host cells, such as the mucosal cells in the human body, for example the intestinal mucosa cells of the gastrointestinal system, the oral or the vaginal mucosa. MVs may therefore relay information, such as probiotic information, from bacterial cells to the host. There is therefore a need for enhancing the production of therapeutic MVs from probiotic bacteria that can be used in probiotic and therapeutic applications. Experimental data as presented herein show that MVs produced by probiotic bacteria could recapitulate the probiotic or therapeutic effects of the probiotic bacteria as illustrated by the effect of isolated MVs on pain signaling and gastrointestinal motility. The MVs not only recapitulated the effects of the probiotic bacteria on pain signaling but were actually more efficient as demonstrated by their ability to act faster than the probiotic bacteria resulting in an earlier onset of the observed effect. This finding was highly unexpected. Experimental data as presented herein also shows that therapeutic MVs isolated from a probiotic bacterial strain had an immune stimulatory effect and were capable of dampening specific cytokines related to autoimmune diseases, and that they also protect the epithelial barrier integrity. Experimental data as presented herein also show that the production of MVs can be induced by a biotic treatment during culture, such as by adding supernatant from another bacterial strain to the probiotic bacterial strain or by co-culturing the probiotic bacteria with a bacteria of another bacterial strain.

The present invention therefore describes protocols that can be used to produce therapeutic MVs, and/or to increase inherent or endogenous production of therapeutic MVs.

An aspect of the embodiments comprises a method of producing therapeutic MVs. The method comprises culturing bacteria of a probiotic bacterial strain in a culture medium and exposing the bacteria to an inducing biotic treatment during culturing to induce production of therapeutic MVs by the bacteria. The probiotic bacterial strain is selected from the group consisting of a *Lactobacillus* strain, a *Bifidobacterium* strain and a combination thereof. The inducing biotic treatment is, in this aspect, selected from the group consisting of co-culturing the bacteria of the probiotic bacterial strain with bacteria of another bacterial strain, culturing the bacteria of the probiotic bacterial strain in presence of a conditioned medium from bacteria of another bacterial strain and a combination thereof. The another bacterial strain is a *Bifidobacterium* strain and the another bacterial strain is different from the probiotic bacterial strain.

Hence, in this aspect, production of therapeutic MVs involves culturing bacteria of the probiotic bacterial strain and at the same time stimulating the bacteria to produce therapeutic MVs by exposing the bacteria to the inducing treatment during culturing to induce production of therapeutic MVs.

Induce production of therapeutic MVs as used herein encompasses stimulating bacteria to produce therapeutic MVs, including promoting, enhancing or increasing production of therapeutic MVs by the bacteria. Alternatively, or in addition, induce production of therapeutic MVs includes more efficient release of the therapeutic MVs from the bacteria, thereby resulting in higher numbers of released therapeutic MVs by the bacteria as compared to when the bacteria are not exposed to the inducing treatment. Alternatively, or in addition, induce production of therapeutic MVs includes the production of more potent or more efficient therapeutic MVs by the bacteria. In such a case, the therapeutic MVs produced by the bacteria exposed to the inducing treatment have enhanced therapeutic effect as compared to MVs produced by non-stimulated bacteria, i.e., bacteria not exposed to the inducing treatment. Hence, the inducing treatment of the embodiments can be used to, for instance, increase production of therapeutic MVs in bacteria of the probiotic bacterial strain that already have an inherent or endogenous production of such therapeutic MVs. In such a case, the inducing treatment boosts this inherent or endogenous MV production of the bacteria, yielding more therapeutic MVs when exposed to the inducing treatment as compared to when not exposed to the inducing treatment. Induce production of therapeutic MVs also encompass inducing production of such therapeutic MVs in bacteria of a probiotic bacterial strain that otherwise do not have any significant MV production when not exposed to the inducing treatment. Hence, inducing production of therapeutic MVs by the inducing treatment encompass both increasing an inherent or endogenous production of therapeutic MVs in bacteria and de novo production of therapeutic MVs in bacteria.

The inducing treatment is, as is further described herein, a treatment of the bacteria that induces, including increases, the production of therapeutic MVs by the bacteria. Hence, by exposing the bacteria to at least one inducing treatment during culturing according to the various embodiments, the bacteria are modified or induced for producing therapeutic MVs.

The culturing of the bacteria can be performed according to a known culturing protocol in a suitable culturing device, fermenter or bioreactor including, but not limited, to stirred-tank bioreactors, airlift bioreactors, hollow-fiber bioreactors and Rotary Cell Culture System (RCCS) bioreactors. The particular culturing conditions are preferably selected based on the particular pro biotic bacterial strain.

In an embodiment, the culture medium comprising the therapeutic MVs and the probiotic bacteria, i.e., the cell slurry, is preserved, such as by drying and/or freezing. Typical examples of drying include spray drying, freeze drying, spray-freeze drying and vacuum drying.

The cell slurry may optionally be concentrated prior to or during preservation to reduce the total volume of the cell slurry and also to concentrate the bacterial cells, therapeutic MVs and any other compounds or agents present therein.

For instance, the cell slurry could be concentrated to a volume corresponding to from about 5 up to 95% of the original volume, such as 5, 10, 15, 20, 25, 30, 35, 40, 45, 50, 55, 60, 65, 70, 75, 80, 85, 90 or 95% of the original volume.

A variety of methods and processes may be employed in order to concentrate the cell slurry. For instance, the cell slurry can be concentrated by removing water and optionally other substances, such as organic acids, sugars and salts from the cell slurry. A filtering device that mainly lets water pass through a filtering membrane may be used. This process is called osmosis and can be run in various operational modes such as reverse osmosis mode, forward osmosis mode. In an embodiment, concentration may also be performed by precipitation of the sample using chemicals. Chemical precipitation can be used to concentrate the cell slurry using the addition of denaturing solvents or salts. Various types of chromatography setups may also be employed for concentration and to separate input samples according to, for instance, their chemical properties and size for example. For instance, size-exclusion chromatography works on the principle of separating samples according to size, trapping smaller molecules into small pores and excluding larger molecules and particles. Ion chromatography assists in separating molecules of certain charges. For example, anion exchange chromatography may be used to exploit the net negative charge found on the bacterial membranes and MVs and bind these to a positively charged chromatographic matrix. These can then be eluted by increasing the ionic strength of the surrounding mobile phase. Another concentration technique is ultrafiltration. Ultrafiltration is based on mechanical rather than chemical interactions. Filtering devices may have a molecular weight cut-off, meaning that everything above a certain molecular weight is retained, while passing through smaller molecules and salt, etc. Usually membranes with highly defined pore sizes are employed. These type of ultrafiltration devices and processes are also employed in different setups, such as Direct Flow Filtration (DFF), or Tangential Flow Filtration (TFF). Tangential flow filtration (TFF), also known as Cross-flow filtration, is different from other filtration systems in that the fluid is passed parallel to the filter, rather than being pushed through a membrane perpendicularly. This method is preferred for its continuous filtration and reproducible performance. The particles that pass through the membrane, the permeate, are put off to the side, while the rest, the retentate, is recycled back to the feed.

In an embodiment, the bacteria are exposed to the inducing treatment during culturing to induce, including to enhance, production of the therapeutic MVs and release of the therapeutic MVs into the culture medium. This means that therapeutic MVs produced by the bacteria of the probiotic bacterial strain following exposure to the inducing treatment are released from the bacteria into the culture medium. In addition, or alternatively, at least some of the therapeutic MVs produced by the bacteria may be associated with and/or attached to the cell membrane and/or cell wall of the bacteria.

In an embodiment, the method comprises isolating the therapeutic MVs from the culture medium, e.g., from the cell slurry or from the conditioned medium. In an embodiment, the isolation of the therapeutic MVs comprises exposing the culture medium, e.g., the cell slurry, to at least one centrifugation at a relative centrifugal force selected within a first interval to obtain a bacteria-depleted supernatant, i.e., the conditioned medium, and exposing the conditioned medium to at least one ultracentrifugation at a relative centrifugal force selected within a second interval to obtain a MV-containing pellet. The second interval is higher than the first interval.

The first or at least one centrifugation at a relative centrifugal force selected within the first interval is performed in order to remove live bacteria and large debris from the culture medium to thereby form a pellet that is discarded and a supernatant that comprises the therapeutic MVs, denoted conditioned medium above. This first step in the isolation process could include a single centrifugation step but preferably comprises at least two centrifugation steps in order to more efficiently remove bacteria and large debris. In the case of at least two centrifugation steps, all may be conducted at the same relative centrifugal force. However, it is generally more efficient to increase the relative centrifugal force for each successive centrifugation step. The first interval is preferably from 100×g to 50 000×g, such as from 200×g to 25 000×g, and preferably from 500×g to 15 000×g. For instance, a first centrifugation step may be at 4 000×g with a second centrifugation step at 10 000×g. Alternatively, a single centrifugation step at 600×g could be used. The supernatant can also, or alternatively, be run through a micron filter (0.20 µm up to 0.50 µm, e.g., 0.45 µm) to remove any debris and/or bacteria that remains from the centrifugations.

The conditioned medium that comprises therapeutic MVs is then exposed to at least one ultracentrifugation at the relative centrifugal force selected within the second interval to obtain a MV-containing pellet. This second step may comprise one or multiple ultracentrifugation steps. In the case of multiple ultracentrifugation steps, all may be conducted at the same relative centrifugal force or the relative centrifugal force may be increased as disclosed above. The second interval is preferably equal to or larger than 75 000×g, such as equal to or larger than 85 000×g, preferably equal to or larger than 100 000×g. For instance, a relative centrifugal force of 118 000×g can be used.

In an embodiment, the isolating step also comprises loading the conditioned medium onto a sucrose gradient or a sucrose cushion and centrifuging at a relative centrifugal force selected within the second interval.

In addition, or alternatively, the conditioned medium may be filtered prior to ultracentrifugation. In such a case, a filter with an average pore size of, for instance, from 0.20 µm up to 0.50 µm could be used.

The isolated therapeutic MVs may be preserved, such as by drying, for instance by spray drying, freeze drying, spray-freeze drying or vacuum drying, and/or freezing. In an embodiment, the therapeutic MVs are stable following preservation for at least 1 month, at least 3 months, at least 5 months or at least 7 months.

The inducing biotic treatment is selected from the group consisting of co-culturing the probiotic bacterial strain with bacteria of another bacterial strain, culturing the probiotic bacterial strain in presence of a conditioned medium from bacteria of another bacterial strain and a combination thereof. The another bacterial strain is preferably a probiotic bacterial strain. For instance, the another bacteria could be of a *Bifidobacterium* strain, preferably a *Bifidobacterium longum* strain, and more preferably *B. longum* DSM 32947 and/or DSM 32948 (deposited by BioGaia AB under the Budapest Treaty at Leibniz-Institut DSMZ-Deutsche Sammlung von Mikroorganismen und Zellkulturen GmbH (Inhoffenstrasse 7B, D-38124 Braunschweig, Germany) on Nov. 1, 2018). The above exemplified *Bifidobacterium* strains are in particular useful in connection with bacteria of a *Lactobacillus* strain as probiotic bacterial strain, and in particular with bacteria of a *L. reuteri* strain, such as *L. reuteri* DSM 17938 (deposited by BioGaia AB under the Budapest Treaty at DSMZ-Deutsche Sammlung von Mikroorganismen und Zellkulturen GmbH (Mascheroder Weg 1 b, D-38124 Braunschweig, Germany) on Jan. 30, 2006) and/or *L. reuteri* DSM 32846 (deposited by BioGaia AB under the Budapest Treaty at DSMZ-Deutsche Sammlung von Mikroorganismen and Zellkulturen GmbH (Inhoffenstr. 7B, D-38124 Braunschweig, Germany) on Jul. 4, 2018).

In a particular embodiment, the bacteria of the probiotic bacterial strain could be co-cultured with bacteria of the another bacterial strain. Alternatively, or in addition, conditioned medium from bacteria of the another bacterial strain could be added to the culture medium comprising bacteria of the probiotic bacterial strain.

In an embodiment, the method also comprises exposing the bacteria to an inducing abiotic treatment during culturing to induce, including increase, production of therapeutic MVs by the bacteria. Hence, in this embodiment, the bacteria are exposed to both an inducing biotic treatment and an inducing abiotic treatment.

Abiotic treatment relates to treatment with non-living chemical and physical components that affect living organisms. Biotic treatment relates to treatment with biotic material, which is either living organisms, or derived from living organisms.

In a particular embodiment, the abiotic treatment is treatment with an abiotic stressor, i.e., an abiotic treatment that induces a stress response in the bacteria of the probiotic bacterial strain when exposed to the abiotic treatment during culturing. The abiotic stressor is, in an embodiment, selected from the group consisting of oxidative stress (oxygen treatment), temperature stress, pH stress, ultraviolet (UV) stress and a combination thereof.

Oxygen treatment means that the bacteria are exposed to increased concentrations of oxygen. In an embodiment, the increased concentration of oxygen is a non-toxic concentration of oxygen. In a particular embodiment, exposing bacteria to an oxygen treatment comprises exposing relative oxygen-tolerant anaerobic bacteria, microaerophilic bacteria, aerobic bacteria and/or facultative anaerobic bacteria to increased oxygen concentrations, i.e., increased non-toxic concentrations of oxygen, during culturing to induce production of therapeutic MVs by the relative oxygen-tolerant anaerobic bacteria, microaerophilic bacteria, aerobic bacteria and/or facultative anaerobic bacteria.

Oxygen treatment as used herein do not involve addition of any reactive oxygen species (ROS), such as peroxides, including hydrogen peroxide, superoxide, or hydroxyl radicals.

Increased oxygen concentration implies a concentration of oxygen in the culture medium that is higher than the (normal) oxygen concentration that is otherwise selected as optimal, or at least suitable, for culturing bacteria of the probiotic bacterial strain, however non-toxic to the bacteria. In one embodiment, the non-toxic concentration of oxygen does not incur significant bacterial cell death, meaning that the exposed bacteria are still viable at least to 70%, preferably at least to 75%, more preferably at least to 80%, such as at least to 85% or 90%, or even higher as compared to when exposing the bacteria to normal oxygen concentrations. This increase in oxygen concentration could be achieved as adding (sparging) oxygen or air to the culture medium in one or multiple bursts or pulses, or during an extended period of time. Alternatively, or in addition, the increase in oxygen concentration can be achieved by agitating or stirring the culture medium comprising the bacteria, including increasing the amount or level of agitation or stirring of the culture medium. The oxygen concentration, e.g., non-toxic concentration, can vary between different bacterial strains, but can typically be set between 0, 1 to 10%. In an embodiment, the oxygen concentration is set to be between 0.5 to 2%. In another embodiment, the oxygen concentration is set to be between 2 to 5%. In yet another embodiment, the oxygen concentration is set to be between 5 to 10%.

A particular aspect of the embodiments comprises a method of producing therapeutic MVs. The method comprises culturing bacteria of a probiotic bacterial strain in a culture medium and exposing the bacteria to an oxidative treatment during culturing to induce production of therapeutic MVs by the bacteria.

Hence, in this aspect of the embodiments, MV production is induced, including increased, in the bacteria by exposing them to an oxygen treatment (oxidative stress) but not necessarily in combination with exposing the bacteria to any inducing biotic treatment.

In an embodiment, the bacteria of the probiotic bacterial strain are selected from the group consisting of relative oxygen-tolerant anaerobic bacteria, microaerophilic bacteria, aerobic bacteria and/or facultative anaerobic bacteria, preferably from the group consisting of aerobic bacteria and facultative anerobic bacteria.

In a particular embodiment, the bacteria are selected from the group consisting of a *Lactobacillus* strain, a *Bifidobacterium* strain and a combination thereof. Preferred *Lactobacillus* and *Bifidobacterium* strains can be selected among the below described illustrative examples of preferred bacterial strains.

Temperature stress may be induced by raising the culture temperature above the normal temperature for culturing the bacteria in the bioreactor, i.e., a so-called high-temperature stress. For instance, if the normal culture temperature is 37° C., the temperature can be increased to at least 42° C., at least 43° C., or at least 44° C., and more preferably at least 45° C., such as at least 46° C., at least 47° C., at least 48° C., at least 49° C. or at least 50° C. Instead of exposing the bacteria to a high-temperature stress, the bacteria may be exposed to a low-temperature stress, i.e., by lowering the culture temperature to below the normal culture temperature. For instance, the culture temperature could be lowered to 10° C., such as 8° C. or less, 6° C. or less, or 4° C. or less.

pH stress may be induced by lowering the pH of the culture medium, in which the bacteria are cultured, from a normal or baseline pH to an acidic or more acidic pH. Alternatively, the bacteria may be temporarily removed from the culture medium, and then exposed to the pH stress, followed by adding the pH stress exposed bacteria to the culture medium or to a fresh culture medium. For instance, the pH may be lowered from a normal pH range of 6.5 to 7 down to a pH of 2 or less.

UV stress may be induced by exposing the bacteria to UV treatment, e.g., by directing UV light into the culture medium comprising the bacteria.

In an embodiment, the method also comprises exposing the bacteria to a stress-inducing agent during culturing to induce, including increase, production of therapeutic MVs by the bacteria. Hence, in this embodiment, the bacteria are exposed to both a stress-inducing agent and an inducing biotic treatment and/or an inducing abiotic treatment.

In an embodiment, the stress-inducing agent is selected from the group consisting of fructose; sucrose; a lysozyme, e.g., from hen egg, also known as muramidase or N-acetylmuramide glycanhydrolase; a mucin, e.g., purified from porcine intestine; a β-lactam, e.g., ampicillin, and a combination thereof.

In a particular embodiment, the stress-inducing agent is sucrose. Sucrose may be added during culturing of the bacteria to induce MV production by said bacteria. For instance, sucrose may be added to the culture medium to obtain a concentration of sucrose within a range of 0.3%-10% in the culture medium, such as 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10%.

The above described examples of inducing treatments may be combined, such as combining multiple, i.e., at least two, abiotic treatments, multiple biotic treatments, treatments with multiple stress-inducing agents, at least one abiotic treatment and at least one biotic treatment, at least one abiotic treatment and treatment with at least one stress-inducing agent, at least one biotic treatment and treatment with at one stress-inducing agent, or at least one abiotic treatment, at least one biotic treatment and treatment with at least one stress-inducing agent.

The duration of the inducing treatment exposure can be selected based on the particular type of treatment, particular probiotic bacterial strain and culturing conditions, such as bioreactor type. For instance, the bacteria may be exposed to an abiotic treatment for 10 min, 15 min, 30 min, 45 min, 1 hour, 1.25 hours, 1.5 hours, 1.75 hours, 2 hours, 2.25 hours, 2.5 hours, 2.75 hours, 3 hours, 3.25 hours, 3.5 hours, 3.75 hours, 4 hours, 4.25 hours, 4.5 hours, 4.75 hours, 5 hours or more as illustrative, but non-limiting, examples. It is also possible to have longer periods of abiotic stress exposure, such as overnight, 12 hours, 18 hours, 24 hours, or even longer. Addition of the stress-inducing agent may comprise adding at least one stress-inducing agent once to the culture medium or at multiple, i.e., at least two, times. Addition of bacteria of another bacterial strain or conditioned medium from such bacteria may also be performed once or at multiple times.

The probiotic bacterial strain is preferably a strain of probiotic lactic acid producing bacteria and is in particular selected from *Lactobacillus* and *Bifidobacterium*. *Lactobacillus* include several species including *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviaries, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii subsp. bulgaricus, L. delbrueckii subsp. delbrueckii, L. delbrueckii subsp. lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamster, L. harbinensis, L. hayakitensis, L. helveticus, L. hilgardii, L. homohiochii, L. iners, L. ingluviei, L. intestinalis, L. jensenii, L. johnsonii, L. kalixensis, L. kefiranofaciens, L. kefiri, L. kimchi, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae,* and *L. zymae.* Preferred examples of such probiotic bacterial strain include *Lactobacillus reuteri, Lactobacillus mucosae, Lactobacillus gasseri* and *Lactobacillus plantarum.* Currently preferred examples of such probiotic bacterial strain include *Lactobacillus reuteri* strains, such as *Lactobacillus reuteri* DSM 17938 and *Lactobacillus reuteri* DSM 32846. Preferred species of *Bifidobacterium* are *B. adolescentis*, *B. breve*, *B. longum*, *B. animalis*, *B. infantis*, *B. thermophilum*, *B. bifidum* and *B. lactis*. A further preferred species of *Bifidobacterium* is *B. longum*. Currently preferred examples of *Bifidobacterium* are *B. longum* DSM 32947 and *B. longum* DSM 32948.

*L. reuteri* is an oxygen-tolerant (alternatively aerotolerant or relative oxygen-tolerant) anaerobe, i.e., can only generate ATP by fermentation.

Further aspects of the embodiments relate to *Bifidobacterium longum* DSM 32947, *Bifidobacterium longum* DSM 32948, and compositions, such as pharmaceutical compositions, nutritional compositions, food supplements and probiotic compositions, comprising *B. longum* DSM 32947 and/or *B. longum* DSM 32948. In a particular embodiment, the bacteria of the bacterial strain, i.e., *B. longum* DSM 32947 and/or *B. longum* DSM 32948, is in a dried or lyophilized form.

Related aspects include probiotic compositions comprising bacteria of a *Bifidobacterium longum* strain selected from the group consisting of *B. longum* DSM 32947, *B. longum* DSM 32948 and a combination thereof and bacteria of another probiotic bacterial strain, preferably of a *Lactobacillus* strain, and more preferably of a *L. reuteri* strain, and in particular a *L. reuteri* strain selected from the group consisting of *L. reuteri* DSM 17938, *L. reuteri* DSM 32846, and a combination thereof.

Further aspects include probiotic compositions comprising a probiotic bacterial strain, preferably of a *Lactobacillus* strain, and more preferably of a *L. reuteri* strain, and in particular a *L. reuteri* strain selected from the group consisting of *L. reuteri* DSM 17938, *L. reuteri* DSM 32846 and a combination thereof, and conditioned medium from the *Bifidobacterium longum* strain selected from the group consisting of *Bifidobacterium longum* DSM 32947, *Bifidobacterium longum* DSM 32948 and a combination thereof.

The bacteria comprised in the probiotic composition according to the above are preferably comprised in the probiotic composition as dried, such as lyophilized or freeze-dried, spray-dried or spray-freeze dried or vacuum-dried bacteria.

Bacteria of *B. longum* DSM 32947 or of *B. longum* DSM 32948 present in the above described probiotic compositions may be provided in dried form, e.g., freeze-dried (lyophilized), spray-dried, spray-freeze-dried or vacuum-dried form. If the compositions also comprise bacteria of another probiotic bacterial strain, such as of *L. reuteri* DSM 17938 and/or *L. reuteri* DSM 32846, these bacteria may also be provided in dried form, such as freeze-dried (lyophilized), spray-dried, spray-freeze-dried or vacuum-dried form, in the compositions.

The *B. longum* DSM 32947 and DSM 32948 have been modified (adapted or evolved) from parent strains through a multi-step selection process to improve growth and decrease a problem with heterogenous growth. Thus, *B. longum* DSM 32947 and DSM 32948 display improved growth. These strains do not occur in nature as they have been forced to evolve, i.e., they are non-native or non-naturally occurring bacterial strains.

The multi-step selection of *Bifidobacterium* from clinical samples involved isolating *Bifidobacterium* isolated from clinical samples on MRS agar plates. To improve the growth and decrease a problem with heterogeneous growth, the bacteria were subjected to the following procedure:

1. Streaking on MRS agar plates and after three days of anaerobic cultivation at 37° C. selecting a colony with good growth;
2. Inoculating the selected colony into MRS broth and incubating it at 37° C. during anaerobic conditions;
3. Taking a sample and repeating step 1 and 2 until the desired characteristics were observed; and
4. Suspending the bacteria in 15% glycerol and stored at −70° C.

The above described treatment improved both the growth and a problem with heterogeneous colony morphology.

By exposing the bacteria to at least one inducing treatment during culturing according to the invention, the bacteria are modified and/or induced to produce, including increase production of, therapeutic MVs and they preferably release these MVs into the culture medium. The inducing treatment relates to alterations in the culturing conditions, which strongly affect the MV production by the bacteria as compared to bacteria not exposed to the inducing treatment during culturing.

To evaluate and/or measure the increased MV production or the altered efficiency of the MVs that has been induced or produced as a result of different inducing treatments, different methods can be applied. An option is to quantify the MVs by, for example, a Nanosight apparatus or by using flow cytometry or by using a fluorescent dye to stain the membrane and thereby quantify the amount MVs. For instance, the fluorescence may be measured (after washing) by using a plate reader (and comparing with a standard curve). A simpler way is also to make a comparison between pellet size of the precipitate or pellet after centrifugation or to measure the weight of the precipitates. Larger pellet size or higher pellet weight means more MVs. Other ways of evaluating the efficiency of the MVs is to measure the activity of the MVs in more complex in vitro models or in vivo models, for instance as disclosed in the Example section.

An important metabolic process in the human body is purine metabolism, in which purines are metabolized and broken down by specific enzymes. An example of such an enzyme is ecto-5'-nucleotidase (CD73), a cell membrane anchored 5'-nucleotidase, which is considered to be a key enzyme in the generation of adenosine. Some probiotic bacteria have a 5'-nucleotidase gene and produce an active 5'-nucleotidase enzyme and are therefore capable of producing adenosine. 5'-nucleotidase activity, and thereby adenosine production, may take place extracellularly, i.e., outside or on the surface of the bacteria, so that it can, for example, be present in the supernatant or other extracellular fluid produced by the bacteria. Thus, an active 5'-nucleotidase enzyme can be present on the cell surface, for example, in the form of a cell wall anchored 5'-nucleotidase, extracellularly from the bacterial cell, for example, in the supernatant and/or as a MV membrane associated 5'-nucleotidase. As a consequence, in this group of bacteria, generation of adenosine and/or activity of a 5'-nucleotidase (EC 3.1.3.5) could be used as a marker for determining the MV production efficiency.

Other possible models include, but are not limited to, models that are currently used to evaluate the probiotic effect of a bacterial strain. For instance, this includes preclinical in vitro models, in which gut motility or pain perception/signalling can be measured, which demonstrates, for example, typical discomforts related to infant colic and other functional gastrointestinal disorders. Several models are used herein to evaluate potential effects on infant colic, for example, the models that are described in Example 1, 3, 4, 9 and 10. It also includes cell-based immune stimulation models, in which selected cytokines can be evaluated. Another mechanism, through which probiotic bacteria exert their effects, is related to decreased mucosal permeability, i.e., to protect the epithelial barrier integrity. The efficiency of MVs can, thus, be measured in an epithelial permeability ETEC (Enterotoxigenic *Escherichia coli*) challenging in vitro model. Also relevant animal models can be used to investigate the effects of the different inducing treatments and also the effects can furthermore be evaluated in a human clinical trial.

The therapeutic MVs may be, optionally following preservation, administered to a mammal, such as in the form of isolated therapeutic MVs, as a probiotic composition as further described here below, or as a processed culture medium, a conditioned medium or cell slurry, such as a dried culture medium, including freeze-dried (lyophilized), spray-dried, spray-freeze-dried or vacuum-dried culture medium, conditioned medium or cell slurry, from the bacteria of the probiotic bacterial strain and the probiotic bacterial strain.

An embodiment relates to a probiotic composition comprising bacteria of a probiotic bacterial strain and therapeutic MVs produced by the probiotic bacterial strain or by another probiotic bacterial strain. The probiotic bacterial strain and the another probiotic bacterial strain are selected from the group consisting of a *Lactobacillus* strain, a *Bifidobacterium* strain and a combination thereof.

In an embodiment, the probiotic bacterial strain or the another probiotic bacterial strain has been exposed to an inducing biotic treatment according to the embodiments. Hence, in an embodiment, the therapeutic MVs in the probiotic composition have been produced by the method of producing therapeutic MVs according to the embodiments. Hence, in an embodiment, the probiotic composition comprises bacteria of a probiotic bacterial strain and therapeutic microvesicles produced by the probiotic bacterial strain or by another probiotic bacterial strain by exposing bacteria of the probiotic bacterial strain or the another probiotic bacterial strain to an inducing biotic treatment during culturing to induce production of the therapeutic microvesicles by the bacteria. The probiotic bacterial strain and the another probiotic bacterial strain are selected from the group consisting of a *Lactobacillus* strain, a *Bifidobacterium* strain, and a combination thereof. The inducing biotic treatment is selected from the group consisting of co-culturing the bacteria with bacteria of another bacterial strain, culturing the bacteria in presence of a conditioned medium from bacteria of another bacterial strain and a combination thereof. The another bacterial strain is a *Bifidobacterium* strain and the another bacterial strain is different from the probiotic bacterial strain and the another probiotic bacterial strain.

In an embodiment, therapeutic MVs are isolated from bacteria of a probiotic bacterial strain, such as described in the foregoing by exposing the bacteria to an inducing treatment during culturing and then isolating the therapeutic MVs from the culture medium. The isolated therapeutic MVs may then be added to isolated bacteria of the same probiotic bacterial strain that was used to produce the therapeutic MVs. In such a case, the probiotic composition comprises a mixture of isolated bacteria of a probiotic bacterial strain and therapeutic MVs isolated from bacteria of the probiotic bacterial strain. In another embodiment, the probiotic composition comprises bacteria of a first probiotic bacterial strain and therapeutic MVs isolated from bacteria of a second, different probiotic bacterial strain. In this latter case it is possible to combine properties or characteristics of different probiotic bacterial strains by mixing isolated bacteria of a probiotic bacterial strain with therapeutic MVs isolated from bacteria from another probiotic bacterial strain. It is also possible to have a probiotic composition comprising bacteria of the first probiotic bacterial strain and therapeutic MVs from bacteria of the first probiotic bacterial strain and therapeutic MVs isolated from bacteria of the second, different probiotic bacterial strain. In another embodiment, the probiotic composition comprises a mixture of at least one bacterial strain and therapeutic MVs from any of the at least one bacterial strain or produced by another bacterial strain.

The bacteria comprised in the probiotic composition according to the above are preferably comprised in the probiotic composition as dried, such as lyophilized or freeze-dried, spray-dried or spray-freeze dried or vacuum-dried bacteria.

As previously described herein, the probiotic bacterial strain is preferably a probiotic lactic acid producing bacterial strain (such as *Lactobacillus*), such as a probiotic *Lactobacillus reuteri* strain, and more preferably *L. reuteri* DSM 17938 and/or *L. reuteri* DSM 32846.

Experimental data presented herein show that therapeutic MVs, produced and isolated from probiotic bacterial strains, were not only able to recapitulate beneficial effects on gastrointestinal motility and pain signaling of the probiotic MV producing bacteria. Importantly, these therapeutic MVs were in fact more efficient than the probiotic bacteria themselves, as demonstrated by the faster onset of the beneficial effects by therapeutic MVs as compared to by the bacteria. Experimental data as presented herein also shows that therapeutic MVs isolated from a probiotic bacterial strain had an immune stimulatory effect. The MVs were capable of reducing specific cytokines related to autoimmune diseases, and they were also shown to protect the epithelial barrier integrity. The experimental data revealed that therapeutic MVs of the embodiments can be used to inhibit, treat or prevent various diseases or disorders that have previously been shown to be inhibited, treated or prevented by the use of probiotic bacteria. In the same manner, the therapeutic MVs can, when administered to a mammal, be expected to produce similar general and/or specific effects, and possibly also improved effects, as compared to the probiotic bacteria when administered to a subject, such as any mammal. Experimental data as presented herein also show that the production of MVs can be induced by a biotic treatment during culture, such as by adding supernatant from another bacterial strain to the probiotic bacterial strain or by adding bacterial cells from a different bacterial strain to the probiotic bacterial strain during culture (so called co-culture). Such inducing biotic treatment generates more efficient or potent MVs in different models as compared to MVs from un-induced or non-stimulated bacterial preparations.

The faster onset of the beneficial effects as seen by the therapeutic MVs may be utilized in the probiotic composition of the embodiments to achieve a prolonged therapeutic effect when administered to a mammal. Thus, therapeutic MVs in the probiotic composition induce or produce an early effect in the mammal due to their faster onset, whereas a later, but typically prolonged, effect is induced or produced by the bacteria of the probiotic bacterial strain comprised in the probiotic composition. Furthermore, the therapeutic MVs may also produce an enhanced therapeutic effect as compared to the therapeutic effect incudec by the bacteria of the probiotic bacterial strain. This means that the probiotic composition of the embodiments achieves significantly improved therapeutic effects in the mammal as compared to merely administered the probiotic bacteria.

In other words, a composition comprising both probiotic bacterial cells and therapeutic MVs provides advantages over compositions with either probiotic bacterial cells or MVs on their own. In a composition comprising both probiotic bacterial cells and therapeutic MVs, the faster onset of beneficial effects, as observed with therapeutic MVs is combined with the prolonged effects of the probiotic bacterial cells to improve the probiotic composition for a fast onset and a prolonged therapeutic effect when administered to a subject, such as a mammal.

Hence, an aspect of the embodiments relates to a probiotic composition comprising a fast-acting component in the form of therapeutic MVs from bacteria of a probiotic bacterial strain. The probiotic bacterial strain is selected from the group consisting of a *Lactobacillus* strain, a *Bifidobacterium* strain and a combination thereof. The probiotic composition also comprises a slow-acting, or prolonged, component in the form of bacteria of the MV producing probiotic bacterial strain or of another probiotic bacterial strain. The another probiotic bacterial strain is selected from the group consisting of a *Lactobacillus* strain, a *Bifidobacterium* strain and a combination thereof. The fast-acting component and the slow-acting component together therefore produce an improved, early onset, and prolonged therapeutic effect when administered to a subject.

In an embodiment, the probiotic bacterial strain or the another probiotic bacterial strain has been exposed to an inducing biotic treatment according to the embodiments. Hence, in an embodiment, the therapeutic MVs in the fast-acting component of the probiotic composition have been produced by the method of producing therapeutic MVs according to the embodiments. Hence, in an embodiment the probiotic composition comprises a fast-acting component in the form of therapeutic microvesicles produced by bacteria of a probiotic bacterial strain by exposing the bacteria to an inducing biotic treatment during culturing to induce production of the therapeutic microvesicles by the bacteria. The probiotic bacterial strain is selected from the group consisting of a *Lactobacillus* strain, a *Bifidobacterium* strain, and a combination thereof. The inducing biotic treatment is selected from the group consisting of co-culturing the bacteria with bacteria of another bacterial strain, culturing the bacteria in presence of a conditioned medium from bacteria of another bacterial strain and a combination thereof. The another bacterial strain is a *Bifidobacterium* strain and the another bacterial strain is different from the probiotic bacterial strain. The probiotic composition also comprises a slow-acting component in the form of bacteria of the probiotic bacterial strain or of another probiotic bacterial strain. The another probiotic bacterial strain is selected from the group consisting of a *Lactobacillus* strain, a *Bifidobacterium* strain, and a combination thereof. The another probiotic bacterial strain is different from the another bacterial strain. The fast-acting component and the slow-acting component together produce a prolonged therapeutic effect when administered to a subject.

In an embodiment, the fast-acting component has an earlier onset of the therapeutic effect in the subject as compared to the slow-acting component. Hence, fast and slow with regard to the fast-acting component and the slow-acting component define relative onsets of the therapeutic effect as induced by these components. In other words, the fast-acting component is a faster or more fast-acting component as compared to the slow-acting component, which could be regarded as a slower or more slow-acting component when compared to the fast-acting component in terms of inducing the therapeutic effect in the subject.

In an embodiment, the fast-acting component is in the form of isolated therapeutic MVs from bacteria of the probiotic bacterial strain.

The discussion presented above with the regard of using the same probiotic bacterial strain or different probiotic bacterial strains for the therapeutic MVs and bacteria also apply to this embodiment. The probiotic compositions of the embodiments can be used as a medicament and in particular be used in treatment of a gastrointestinal disorder.

An aspect of the embodiments defines a probiotic composition comprising bacteria of a probiotic bacterial strain and therapeutic MVs produced by the probiotic bacterial strain or by another bacterial strain for use as a medicament and in particular for use in treatment of colic. An aspect of the embodiments also defines a probiotic composition comprising the above described fast-acting component and the slow-acting component for use as a medicament and in particular for use in treatment of colic.

In an embodiment, the colic is infant colic (also referred to as infantile colic).

Other aspects of the embodiments define the probiotic composition comprising the bacteria of the probiotic bacterial strain and the therapeutic MVs produced by the probiotic bacterial strain or by another bacterial strain or the probiotic composition comprising fast-acting component and the slow-acting component for use in treatment of a disease selected from the group consisting of an infant or childhood gastrointestinal disorder or disease, a gastrointestinal pain disorder, a bone loss disease a periodontal disease, and a combination thereof.

The therapeutic MVs may be produced by bacteria of the same probiotic bacterial strain as are included in the probiotic composition. Alternatively, or in addition, therapeutic MVs may be produced by bacteria of another probiotic bacterial strain than the bacteria included in the probiotic composition.

In an embodiment, the bacteria of the probiotic bacterial strain in the probiotic composition has been exposed to the inducing biotic treatment according to the embodiments.

The therapeutic MVs isolated from bacteria of a probiotic bacterial strain can be used in treatment of colic, such as infant colic. The probiotic bacterial strain is selected from the group consisting of a *Lactobacillus* strain, a *Bifidobacterium* strain and a combination thereof.

The embodiments also relates to therapeutic MVs isolated from bacteria of a probiotic bacterial strain can be used in treatment of a disease selected from the group consisting an infant or childhood gastrointestinal disorder or disease, a gastrointestinal pain disorder, a bone loss disease a periodontal disease, and a combination thereof. The probiotic bacterial strain is selected from the group consisting of a *Lactobacillus* strain, a *Bifidobacterium* strain and a combination thereof.

The therapeutic MVs are preferably from a *Lactobacillus reuteri* strain and even more preferably from *Lactobacillus reuteri* DSM 17938 and/or *Lactobacillus reuteri* DSM 32846.

The isolated therapeutic MVs or the therapeutic MVs in the probiotic composition have preferably been produced by bacteria of a probiotic bacterial strain exposed to an inducing biotic treatment as disclosed herein. An embodiment relates to therapeutic microvesicles isolated from bacteria of a probiotic bacterial strain exposed to an inducing biotic treatment during culturing to induce production of the therapeutic microvesicles by the bacteria. The probiotic bacterial strain is selected from the group consisting of a *Lactobacillus* strain, a *Bifidobacterium* strain, and a combination thereof. The inducing biotic treatment is selected from the group consisting of co-culturing the bacteria with bacteria of another bacterial strain, culturing the bacteria in presence of a conditioned medium from bacteria of another bacterial strain and a combination thereof. The another bacterial strain is a *Bifidobacterium* strain and wherein the another bacterial strain is different from the probiotic bacterial strain.

In an embodiment, the probiotic composition and/or therapeutic MVs may alternative be used to treat a gastrointestinal disorder. The gastrointestinal disorder is preferably a functional gastrointestinal disorder selected from the group consisting of a functional esophageal disorder, such as functional heartburn, functional chest pain of esophageal origin, functional dysphagia and globus; a functional gastroduodenal disorder, such as functional dyspepsia, aerophagia, unspecified excessive belching, chronic idiopathic nausea, functional vomiting, cyclic vomiting syndrome and rumination syndrome; a functional bowel disorder, such as irritable bowel syndrome (IBS), functional constipation, functional diarrhea and unspecified functional bowel disorder; functional abdominal pain syndrome, such as functional abdominal pain (FAP), a functional gallbladder and sphincter of Oddi disorder, such as functional gallbladder disorder, functional biliary sphincter of Oddi disorder and functional pancreatic sphincter of Oddi disorder; a functional anorectal disorder, such as functional fecal incontinence, functional anorectal pain and functional defecation disorder; a childhood functional gastrointestinal disorder, such as infant regurgitation, infant rumination syndrome, cyclic vomiting syndrome in infants, functional diarrhea, infant dyschezia and functional constipation.

In a particular embodiment, the gastrointestinal disorder is selected from the group consisting of a gastrointestinal motility disorder, gastrointestinal pain, colic, irritable bowel syndrome, and constipation.

In an embodiment, the infant or childhood gastrointestinal disorder or disease is an infant gastrointestinal disorder or disease, such as an infant functional gastrointestinal disorder or disease. In a particular embodiment, the infant gastrointestinal disorder or disease is selected from the group consisting of an infant gastrointestinal motility disorder, infant gastrointestinal pain, infant colic, infant irritable bowel syndrome, food intolerance in infants, infant constipation, infant diarrhea, infant regurgitation, infant rumination syndrome, infant dyschezia, functional constipation in infants and a combination thereof.

In another particular embodiment, the infant gastrointestinal disorder or disease is selected from the group consisting of infant colic or food intolerance in infants and a combination thereof.

In another particular embodiment, the infant gastrointestinal disorder or disease is an infant gastrointestinal motility disorder, preferably infant constipation and/or infant diarrhea and a combination thereof.

In another particular embodiment, the infant gastrointestinal disorder or disease is an infant gastrointestinal motility disorder and/or infant colic.

In an embodiment, the infant or childhood gastrointestinal disorder or disease is childhood gastrointestinal disorder or disease, such as an childhood functional gastrointestinal disorder or disease.

In a particular embodiment, the childhood gastrointestinal disorder or disease is selected from the group consisting of childhood regurgitation, childhood rumination syndrome, functional diarrhea in children, childhood dyschezia, functional constipation in children, and a combination thereof.

In another particular embodiment, the childhood gastrointestinal disorder is selected from the group consisting of childhood regurgitation, childhood dyschezia, and a combination thereof.

In an embodiment, the gastrointestinal pain disorder is selected from the group consisting of functional abdominal pain (FAP), abdominal colicky pain, frequent recurrent abdominal pain (FRAP), and a combination thereof.

In an embodiment, the bone loss disease is selected from the group consisting of osteoporosis, osteopenia, and a combination thereof.

In an embodiment, the probiotic compositions are for use in the treatment of osteoporosis or osteopenia.

In an embodiment, the periodontal disease is selected from the group consisting of periodontitis, gingivitis and a combination thereof.

In another embodiment, the probiotic compositions are for use in the treatment or periodontitis.

In a further particular embodiment, the gastrointestinal motility disorder is selected from the group consisting of abdominal distention, recurrent obstruction, abdominal colicky pain, constipation, gastroesophageal reflux disease, intractable, recurrent vomiting, diarrhea, inflammatory bowel disease (IBD), fecal incontinence, frequent recurrent abdominal pain (FRAP), regurgitation or food intolerance.

The embodiments also relate to use of a probiotic composition or therapeutic MVs isolated from a probiotic bacterial strain as a medicament and for the manufacture of a medicament for the treatment of a gastrointestinal disorder.

The embodiments further encompass a method of inhibiting, treating or preventing a gastrointestinal disorder. The method comprises administering a probiotic composition or therapeutic MVs isolated from a probiotic bacterial strain to a subject to inhibit, treat or prevent the gastrointestinal disorder.

Experimental data as presented herein also shows that therapeutic MVs isolated from a probiotic bacterial strain had an immune stimulatory effect and were capable of dampening IFN-γ and IL-17A secretion. Also effects in increased IL-6 secretion was observed. Thus, such therapeutic MVs can be used as modulators of human immunity.

Probiotic compositions of the invention and/or therapeutic MVs according to the invention could be used to dampen or lower the amount of the cytokines IFN-γ and/or IL-17A when administered to a subject. Accordingly, the probiotic compositions and/or therapeutic MVs may be used in inhibiting, treating or preventing diseases characterized by aberrant expression of IFN-γ and/or IL-17A including inflammatory, autoinflammatory and autoimmune diseases. In a particular embodiment, the inflammatory, autoinflammatory and autoimmune disease is selected from the group consisting of SLE, MCTD, RA, SS, DM, SSc, MS, psoriasis, bone loss, osteoporosis, osteopenia, periodontitis, gingivitis, sarcopenia, cachexia, malnutrition and allergy, such as AD, AR, and asthma, as well as food intolerance and allergy.

Probiotic compositions of the invention and/or therapeutic MVs according to the invention could be used to increase the secretion of the cytokine IL-6 when administered to a subject. IL-6 is a pleiotropic cytokine with a variety of functions in the body. Most such functions and processes are linked to inflammatory responses, however these functions and responses are important for e.g. protection against pathogens. However, the proinflammatory processes in the body have to be well balanced and *L. reuteri* DSM 17938 has also been described to increase the amount of regulatory T cells (e.g. Liu, Y., Fatheree, N. Y., Dingle, B. M., Tran, D. Q., & Rhoads, J. M. (2013). *Lactobacillus reuteri* DSM 17938 changes the frequency of Foxp3+ regulatory T cells in the intestine and mesenteric lymph node in experimental necrotizing enterocolitis. PloS One, 8(2), e56547. http://doi.org/10.1371/journal.pone.0056547). An increased expression of IL-6 in combination with higher frequency of regulatory T cells could be a way to make the immune system more alert and improve the infection protection without increasing the risk for inflammation. Accordingly, the probiotic compositions and/or therapeutic MVs may be used to balance the anti- and pro-inflammatory processes of the immune system.

Enterotoxigenic *Escherichia coli* (ETEC) is a type of *E. coli* and one of the leading bacterial causes of diarrhea in the developing world, as well as the most common cause of travelers' diarrhea. It is estimated that about 157,000 deaths occur each year, mostly in children, from ETEC. The main hallmarks of ETEC are expression of one or more enterotoxins and presence of fimbriae used for attachment to host intestinal cells.

Experimental data as presented herein shows that therapeutic MVs isolated from a probiotic bacterial strain protected the epithelial barrier integrity from the detrimental effect of ETEC, which is a model for studying the effects of epithelial permeability. The main function of the intestinal barrier is to regulate the absorption of nutrients, electrolytes and water from the lumen into the circulation and, on the other hand, to prevent the passing of pathogenic microorganisms and toxic luminal substances into the circulation, an intact barrier is thus essential for obtaining a healthy condition. A disrupted intestinal barrier is associated with several diverse diseases and conditions, such as irritable bowel syndrome (IBS), Crohn's disease, depression, autism spectrum disorders, diverticular disease, periodontitis, osteopenia and osteoporosis.

It has also been reported that intestinal barrier alterations may be a main driver of several cachectic features (Bindels et al. (2018)).

The epithelial barrier integrity is not only important in the intestine, an intact barrier is of importance also in the oral cavity for example. The gingival epithelium is the first in line of defense in the oral cavity against microbial assault. If disrupted, bacteria collectively get access to the underlying connective tissue which can lead to inflammation and destruction of the attachment apparatus of the tooth (DiRienzo (2014)). Accordingly, the probiotic compositions and/or therapeutic MVs may be used in inhibiting, treating or preventing diseases or conditions causing a disruption in epithelial barrier integrity, i.e., epithelial barrier dysfunction, including IBS, Crohn's disease, cachexia, osteopenia, osteoporosis, gingivitis, periodontitis, depression, autism spectrum disorders, diverticular disease and/or inhibiting, treating or preventing ETEC infection and in inhibiting, treating or preventing diarrhea and/or travelers' diarrhea caused by ETEC or other pathogenic bacteria.

The faster onset of the medical or probiotic effect as seen by therapeutic MVs as compared to probiotic bacteria could be useful in treating subjects suffering from a disease or disorder, such as a gastrointestinal disorder, an inflammatory, autoinflammatory or autoimmune disease, an epithelial barrier dysfunction, an ETEC infection, diarrhea and/or travelers' diarrhea. This means that by administering therapeutic MVs or a probiotic composition comprising such therapeutic MVs then a faster onset of the therapeutic, such as medical or probiotic, effect can be obtained as compared to merely administering the probiotic bacteria. The different timings in onsets of the medical or probiotic effects as seen between therapeutic MVs and probiotic bacteria can also be utilized as mentioned in the foregoing to achieve a prolonged medical or probiotic effect in the subject. Thus, therapeutic MVs administered to the subject will contribute to a fast or immediate therapeutic effect in the subject, whereas probiotic bacteria administered, either separately or together with the therapeutic MVs, to the subject will contribute to a slower or delayed therapeutic effect in the subject. As a consequence, by administering both therapeutic MVs and probiotic bacteria, either separately or together, to the subject a prolonged medical or probiotic effect, i.e. both immediate and delayed, can be obtained.

An appropriate mode of administration and formulation of the probiotic composition or therapeutic MVs can be selected based on the disease or disorder. A preferred mode of administration is oral. Other modes of administration include nasal, intraocular, topical or some other form of local administration to the skin, rectum, nose, eyes, vagina or gums, or intravenous, subcutaneous or intramuscular injection.

Appropriate doses of the probiotic composition or therapeutic MVs as defined herein can readily be chosen depending on the disease or disorder to be treated, the mode of administration and the formulation concerned. For example, a dosage and administration regime is selected to ensure that the therapeutic MVs or probiotic composition, administered to the subject in accordance with the present invention, can result in desired therapeutic effects, prophylactic effects or health benefits. Thus, preferably the dosage is a therapeutically or prophylactically effective dosage, which is appropriate for the type of subject and disease or disorder being treated. For example, daily doses of $10^4$ to $10^{10}$, for example $10^5$ to $10^9$, or $10^6$ to $10^8$, or $10^8$ to $10^{10}$ total CFUs of bacteria may be used. A preferred daily dose is around $10^8$ total CFUs, e.g., $10^7$ to $10^9$ or $10^8$ to $10^9$ CFUs of bacteria. For example, daily doses of $10^4$ to $10^{14}$, for example $10^5$ to $10^{13}$, or $10^6$ to $10^{12}$, or $10^8$ to $10^{12}$, or $10^{10}$ to, $10^{12}$, or $10^{10}$ to $10^{14}$ total number of therapeutic MVs may be used. A preferred daily dose is around $10^{10}$ total number of therapeutic MVs, e.g., $10^9$ to $10^{11}$ or $10^{10}$ to $10^{11}$ therapeutic MVs. Another preferred daily dose is around $10^9$ total number of therapeutic MVs, e.g., $10^8$ to $10^{10}$ therapeutic MVs. Another preferred daily dose is around $10^8$ total number of therapeutic MVs, e.g., $10^7$ to $10^9$ therapeutic MVs. Another example would be to use the MVs produced by a fixed number of bacteria, such as $10^8$ or $10^9$ CFUs of bacteria.

The present invention also relates to methods for inhibiting, treating or preventing colic, in particular infant colic, and/or a disease selected from the group consisting of an infant or childhood gastrointestinal disorder or disease, a gastrointestinal pain disorder, a bone loss disease, a periodontal disease, and a combination thereof in a subject. The method comprises administering a probiotic composition and/or therapeutic MVs according to the invention to the subject.

Inhibiting a disease or disorder as used herein encompass delaying the onset of the disease or disorder, or a symptom associated with the disease or disorder.

The subject is preferably a mammal subject, and more preferably a human subject.

Examples as disclosed herein describe protocols for production and isolation of therapeutic MVs from the well-studied *L. reuteri* DSM 17938 bacterial strain with the purpose of investigating and utilizing the probiotic effect of the probiotic bacterial strain and its therapeutic MVs. The probiotic effect of isolated MVs was compared to that of the whole bacteria. It was found that the MVs are able to recapitulate the beneficial effects of the whole bacteria in an ex vivo model to study gastrointestinal motility and in an in vitro model to study pain signaling. Surprisingly, the MVs did not only recapitulate the bacterial probiotic effect, but that they were even more efficient as compared to whole bacteria as demonstrated by their ability to act faster in a nerve signaling model, which resulted in an earlier onset of the observed effect. To even further strengthen the results, another *L. reuteri* strain (*L. reuteri* DSM 32846) was investigated, which also showed similar effects. Furthermore, the effect of *L. reuteri* DSM 17938 and *L. reuteri* DSM 32846 could be further improved when the bacteria were subjected to inducing treatments, including co-culturing experiments with certain other bacterial strains or with conditioned medium from other bacterial strains, which enhanced the ability of the bacteria to produce and release MVs.

In order to study therapeutic MVs from probiotic bacterial strains and their effect in different physiological models, isolated MV fractions were isolated by culturing bacteria followed by isolation of released MVs. The inventors have identified improved ways to culture probiotic bacteria for increased production of MVs that retain and also show an enhanced biological activity.

EXAMPLES

Example 1—Alteration in Enzymatic Activity Associated with MV Production

*Lactobacillus reuteri* DSM 17938 was cultured and subjected to different inducing treatments at specific time points. The response to these inducing treatments was determined using an enzymatic assay and compared to the response obtained with control treatments. The inducing treatments involved inducing stress onto the bacteria during their growth phase, and the effect on enzymatic activity was then measured in the bacterial conditioned medium.

Materials and Methods

Culturing/Sample Collection

*L. reuteri* DSM 17938 was inoculated from frozen stock in 25 mL de Man-Rogosa-Sharpe (MRS) medium under normal culturing conditions, i.e., anaerobically cultured at 37° C. overnight. Then, the bacteria (20 mL) was re-inoculated in 200 mL MRS and different inducing treatments were applied, as described in more details below. The bacterial samples were centrifuged at 5000×g for 10 min, the supernatants were transferred to a new tube, then centrifuged at 10,000×g for 10 min. The supernatants were filtered through a 0.45 µm filter, and kept on ice before further centrifuging using an ultracentrifuge at 32 000 rpm at 4° C. for 3 h (Beckman SW 32 Ti Rotor, Swinging bucket, 30 mL tubes). The supernatants were discarded (gently poured out, with help of pipette). The pellets were carefully resuspended in resuspension media (phosphate buffered saline (PBS)). The resuspension volume varied, between 100-300 µL, depending on the pellet size. The samples were aliquoted and stored at −70 C.

Oxygen Treatment

Increased oxygen concentrations (oxidative stress) was simulated by intense shaking of the bacterial culture. The oxidative stress simulation was continuously kept on shake for 24 hours.

High Temperature Treatment

Temperature-induced stress was induced by raising the temperature from T=37° C. to T=50° C. at the time point when the optical density (OD) reached around 1.6 absorbance and kept at T=50° C. for 20 minutes. After this high temperature treatment, the bacteria were cultured at normal conditions at T=37° C. Total culturing time was 24 hours.

Figure 1:
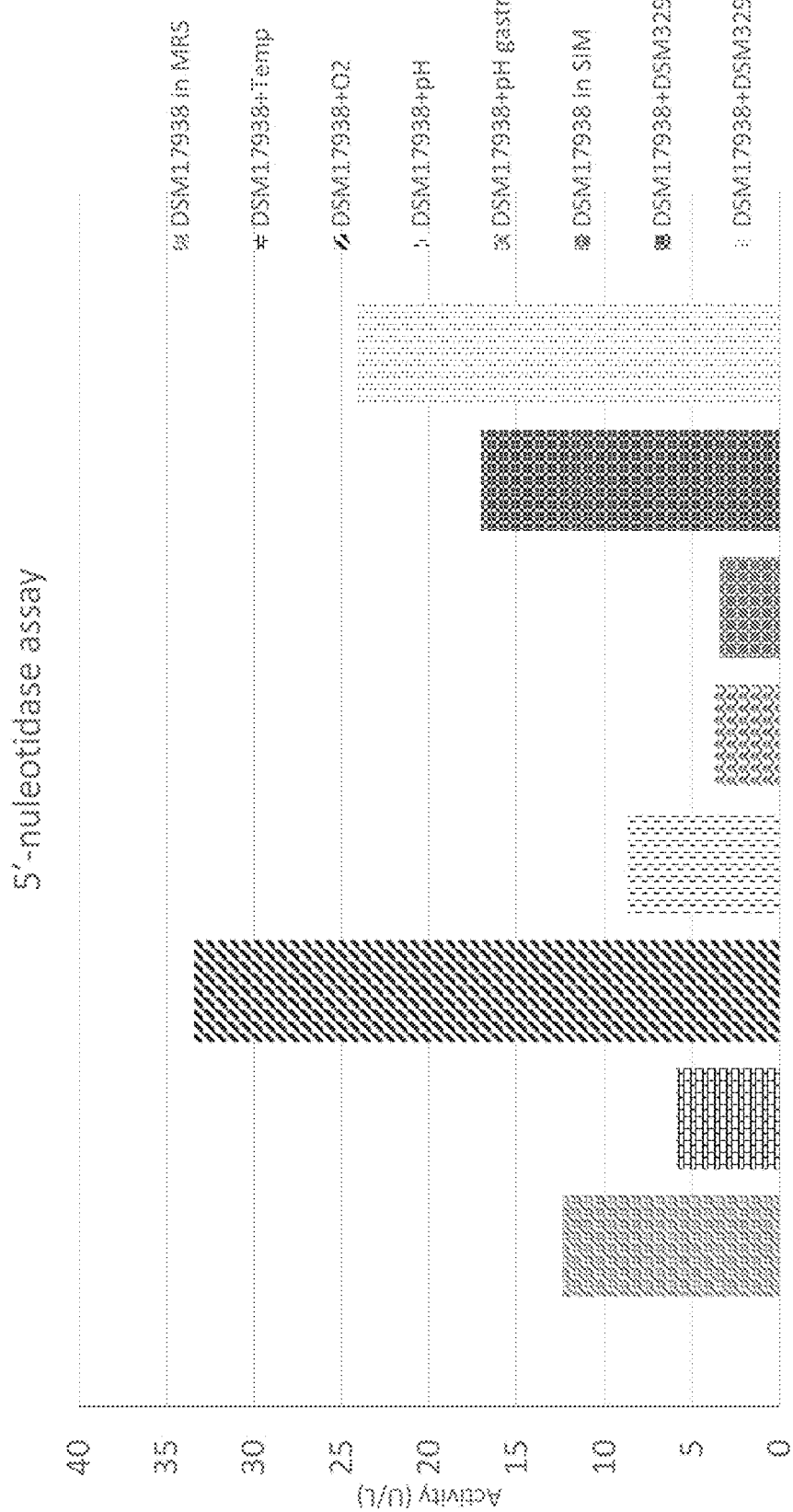
FIG. 1 shows measurements of the 5'-nucleotidase activity in a conditioned medium following exposure of *Lactobacillus reuteri* DSM 17938 to different inducing treatments.

Shift in pH Treatment pH-induced stress was induced by lowering the pH from pH 6.5 to pH 2 at the time point when the optical density (OD) reached around 1.6 absorbance. The pH shift was obtained by spinning down the bacterial cells and adding simulated gastric juice to the bacterial pellet to reach pH 2. The reduced pH was kept for 10 minutes before the supernatant was added back to the bacterial cells to normalize the pH to 6.5. Culturing time varied due to that two different samples were taken. They were named differently as shown in FIG. 1. pH: Sample was taken after 24 h cultivation time; pH+gastric fluid: Sample was taken directly after 10 min induction of gastric fluid.

Co-Culture Treatment

In this treatment, *L. reuteri* DSM 17938 was co-cultured with *Bifidobacterium longum* DSM 32947 and *B. longum* DSM 32948 in SIM (simulated intestinal media, recipe as described below) by the addition of supernatant, i.e., conditioned medium, from *B. longum* DSM 32947 or *B. longum* DSM 32948. As a control, *L. reuteri* DSM 17938 was grown in SIM.

TABLE 1

| recipe for the SIM (simulated intestinal media) Simulated intestinal media (per litre) |
|---|
| 2 g tryptone (Oxoid) |
| 2 g yeast extract |
| 1.0 g NaCl |
| 0.5 g $K_2HPO_4$ |
| 0.5 g $KH_2PO_4$ |
| 0.1 g $MgSO_4 \times 7 H_2O$ |
| 0.01 g $CaCl_2 \times 2 H_2O$ |
| 5.58 g MOPS |
| 1 ml Tween 80 |
| 2.5 mg Hemin (1.0 mg/ml, 2.5 ml; solved in 0.05M NaOH) |
| 1 mg Vitamin K (vitamin $K_2$; 2 mg/ml, 0.5 ml; solved in ethanol) |
| 0.4 g Cystein-HCl |
| 0.5 g bile (porcine) |
| 0.005 g $FeSO_4 \times 7 H_2O$ |
| 0.05 g $MnSO_4$ |
| 100 ng $CoCl_2 \times 6 H_2O$ (100 µg/ml, 1 ml) | pH was adjusted to 6.8; autoclaved at 121° C. for 15 min. Sterile filtered sugar and electron acceptor solutions were added before inoculation. Final concentrations: 15 mM of each. Sugar: Galacto-oligosaccharides (GOS) or glucose. Electron acceptor: Citrate, 1,2 propanediol or fructose.

Enzymatic Activity

The samples obtained from the inducing treatments above were thawed and then tested in a 5'-nucleotidase activity assay using the Crystal Chem 5'-Nucleotidase Assay Kit (Crystal Chem, Elk Grove Village, Ill., USA). In short, the procedure was performed in two steps. Firstly, reagent 1 (CC1) containing AMP was added to the supernatant samples to convert AMP to adenosine by any 5'-nucleotidase enzyme present in the supernatant samples. Adenosine was further hydrolysed into inosine and hypoxanthine by components in reagent 1. In the second step, reagent 2 (CC2) was added to convert hypoxanthine into uric acid and hydrogen peroxide, which was used to generate a quinone dye that was measured kinetically at 550 nm in a spectrophotometer. The 5'-nucleotidase activity in the samples was determined by calculating the change in absorbance between 3 and 5 minutes and comparing with the value from a calibrator sample.

Results

As can be seen from the results presented in FIG. 1, the 5'-nucleotidase activity was increased by oxygen treatment (DSM17938+O2) and co-culture of *L. reuteri* DSM 17938 and *B. longum* DSM 32947 or *B. longum* DSM 32948 in SIM media (DSM17938+DSM32947 in SIM or DSM17938+DSM32948 in SIM).

Other inducing treatments did not induce any increase in 5'-nucleotidase activity compared to control grown *L. reuteri* DSM 17938 (DSM17938 in MRS media or DSM17938 in SIM media).

Example 2—Specific Culturing Conditions is Associated with an Increased MV Production

*Lactobacillus reuteri* DSM 17938 was cultured and subjected to different inducing treatments. The amount of MV produced as a result to these inducing treatments was determined using a Nanoparticle Tracking Analysis (NTA) and the results were compared to the response obtained with control treatments. The inducing treatments involved oxygen treatment and sucrose treatment, and the effect on the MV production was then measured in the bacterial conditioned medium.

Materials and Methods

Oxygen Treatment

*L. reuteri* DSM 17938 was cultured under normal culturing conditions, i.e., anaerobically cultured in de Man-Rogosa-Sharpe (MRS) medium at 37° C. in a bottle/flask. Oxygen treatment was induced by intense shaking of the bacterial culture for 24 hours. As a control *L. reuteri* DSM 17938 was cultured under normal culturing conditions, i.e., anaerobically cultured in MRS medium at 37° C. in a bottle/flask without increasing oxygen concentration (no oxygen treatment).

Sucrose Treatment

*L. reuteri* DSM 17938 was cultured under normal culturing conditions, i.e., anaerobically cultured in *Lactobacillus* Carrying Medium (LCM) medium at 37° C. in a bottle/flask. Stress was induced by adding sucrose (2% final concentration in LCM) to the bacterial culture at the start of fermentation. The total culturing time was 24 hours. As a control, *L. reuteri* DSM 17938 was grown under normal culturing conditions with the addition of glucose 2% instead of sucrose 2%.

Nanoparticle Tracking Analysis (NTA)

The physicochemical characterization of MV was investigated by using the NTA. MVs were suitably diluted with particle-free PBS (0.02 μm filtered) to obtain a concentration within the recommended measurement range ($1\text{-}10 \times 10^8$ particles/ml), and directly tracked using the NanoSight NS300 system (NanoSight™ technology, Malvern, United Kingdom). The analysis was carried out according to the following instrumental set up:

1. Sample loading: Loading the sample with syringe pump into the O-Ring top-plate, which was mounted on the laser module (laser beam of 488 nm).
2. Sample measurement: After optimizing the image, videos were collected at 25° C. with high-sensitivity sCMOS camera and analyzed using the NTA software (version 3.2) after capture in script control mode (3 videos of 90 s per measurement) using syringe pump speed 50.
3. Sample analysis: Samples were captured and analyzed by applying instrument-optimized settings, which is the best visualization of particles by applying software adjustments (camera level, focus and detection threshold) in order to optimize analysis results with respect to different samples. Further settings, such as blur, minimum track length and minimum expected size were set to "automatic" and viscosity to 0.890 cP. The NTA software was optimized and then tracked each particle on a frame-by-frame basis, and its brownian movement tracked and measured frame to frame by capturing a video file. The software tracked many particles individually and using the Stokes-Einstein equation calculated their hydrodynamic diameters. Multiple videos of 90 s duration were recorded generating replicate histograms that were averaged for each sample.

Results

Both oxygen treatment and the addition of sucrose resulted in an increase in MV production compared to the corresponding controls, see Table 2 below.

TABLE 2

| Sample | MV production MVs/ml |
|---|---|
| *L. reuteri* DSM 17938 in MRS | $2.6 \times 10^8 \pm 3.0 \times 10^7$ |
| *L. reuteri* DSM 17938 in MRS and oxygen treatment | $1.4 \times 10^{10} \pm 4.5 \times 10^8$ |
| *L. reuteri* DSM 17938 in LCM | $2.5 \times 10^7$ |
| *L. reuteri* DSM 17938 in LCM and addition of sucrose 2% | $4.7 \times 10^7$ |

Example 3—Isolated Bacterial Microvesicles Recapitulate the Effect of the Bacteria on Gut Motility Materials and Methods Animals Adult male Swiss Webster mice (6-8 weeks) were obtained from Charles River Laboratories (Wilmington, MA, USA). Animals were housed 4-5/cage on a 12-hour light/dark cycle and provided food and water ad libitum. The subsequent procedures took place in vitro, following cervical dislocation in accordance with the McMaster Animal Ethics Research Board (AREB) (permit 16-08-30).

Tissue Flotation Bath Recordings

The tissue flotation bath recordings were performed as described in Wu et al. (2013). A minimum of four-centimeter long jejunum and colon segments were extracted and mounted within a 20 mL tissue flotation bath filled with oxygenated Krebs at 34° C. The oral end of the segments was cannulated and the contents were flushed from the lumen by gravity perfusion with carbogen-gassed Krebs using Mariotte bottles. Once clear, the anal end of the segments was cannulated to the silicon outflow tube. The intraluminal compartment was perfused with room temperature Krebs at 5 ml/min. The serosal compartment was perfused by 34° C. heated carbogen-gassed Krebs at a rate of 2 ml/min. Oxygenated Krebs was composed of (mmol $L^{-1}$): 118 NaCl, 4.8 KCl, 25 $NaHCO_3$, 1.0 $NaH_2PO_4$, 1.2 $MgSO_4$, 11.1 glucose, and 2.5 $CaCl_2$) bubbled with carbogen gas (95% $O_2$ and 5% $CO_2$). Prior to recording, the intraluminal pressure was adjusted to 2-3 hPa by increasing and decreasing the heights of the inflow and outflow tubes. Treatments were applied by opening and closing the respective stopcocks to stop intraluminal flow of Krebs and begin flow of bacteria. The *L. reuteri* DSM 17938 was applied at a concentration of 8-log colony-forming units (CFU)/mL. The conditioned medium from *L. reuteri* DSM 17938, microvesicles produced by *L. reuteri* DSM 17938 and conditioned medium with the microvesicles removed were applied at concentrations equal to that of the whole bacteria.

Video Recording

Videos were recorded using a JVC video webcam placed 7 cm above the tissue segment. The video clips were recorded and saved in a MOV file format at a frame rate of 10 fps and an aspect ratio of 4:3 using NCH Debut Video Capture. Recording duration varied from 20 minutes to 40 minutes. Using VideoPad Video Editor, the videos were zoomed to four centimeters using a forced aspect ratio of 4:3. The video was converted to black and white by adjusting the color curves and applying a two-tone filter. The black and white video was exported at 10 fps at a resolution of 400×300 pixels.

Analysis

All generation, manipulation, and analysis of spatiotemporal diameter maps were performed as described in Wu et al. (2013). The video recordings were analyzed using an StMap plugin for NIH Image J software. Using an edge detection routine, the diameter of each position across the gut was represented as a hue value from 0 to 255. Contractions of the gut where the diameter is smaller, approach a hue value of 0, and are represented as darker black areas. Areas of dilation or relaxation approach a hue value of 255 and are white. The software generates a spatiotemporal map throughout the duration of the video. The map displays alternating dark and light hues based on position along the gut, time, and diameter. The spatiotemporal map runs oral to anal on the vertical axis and across time on the horizontal axis. Propagating contractile complexes (PCC) velocity was determined by measuring the slope of the large dark contractions. PPC frequencies were determined by measuring the number of contractions between intervals. Amplitude was measured as the height (gut diameter) of peak contractions.

Bacteria

15 *L. reuteri* DSM 17938 from stock were grown in de Man-Rogosa-Sharpe (MRS) medium, harvested at 48 to 72 h, washed in phosphate-buffered saline (PBS), and stored at −20° C. in aliquots of 1.1 ml at $1\times10^{10}$ CFU/mL, and its microvesicles isolated as described below.

MVs were isolated from *L. reuteri* DSM 17938 broth culture (48-72 h). After centrifugation at 600×g for 30 min, supernatants were filtered through 0.22 µm filters, washed twice in PBS at 100,000×g at 4° C., resuspended in sterile PBS corresponding in volume of initial *L. reuteri* DSM 17938 culture, and stored at −80° C. in 0.5 ml aliquots representing $1\times10^{12}$ CFU/ml. MVs were quantified by reference to the number of viable bacteria in the culture and also standardized by protein content (consistently 5-8 mg/ml protein, 25-60 ng/ml DNA, and 18-30 ng/ml RNA; n=10) measured by NanoDrop ND-1000 (NanoDrop Technologies, Wilmington, Del., USA). MV preparations were used at an equivalent of $10^{10}$ CFU/ml throughout experiments unless otherwise stated.

Bacteria were diluted to a concentration of 8-log CFU/mL for use.

Results

*L. reuteri* DSM 17938 and the products of its cultivation were applied intraluminally to in vitro preparations of mouse jejunum and colon to determine whether microvesicles produced by *L. reuteri* DSM 17938 could replicate the effect of the parent bacteria on intestinal motility. The conditioned media (CM) was defined as the growth media (broth), in which *L. reuteri* DSM 17938 bacteria had been cultivated. The bacteria were separated from the CM by centrifugation and the remaining CM was applied intraluminally to the in vitro intestinal preparations as described above. Microvesicles (MV) were isolated by centrifugation from *L. reuteri* DSM 17938 cultivated for 72 hours, then resuspended in Krebs buffer. The remaining conditioned media after the microvesicles and bacteria had been removed (CM-MV) was then administered intraluminally to the tissue. As a negative control, the growth media used to culture the bacteria (broth) was applied separately. The effect of these treatments was compared to Krebs buffer control and measured across three parameters of propagating contractile complexes (PCC) in the gut segments: velocity, frequency, and amplitude.

The results were confidently reproduced with 24 hours preparations.

*L. reuteri* DSM 17938 and its Products Decreased Small Intestinal Motility

Jejunal PCC Velocity

Figure 2:
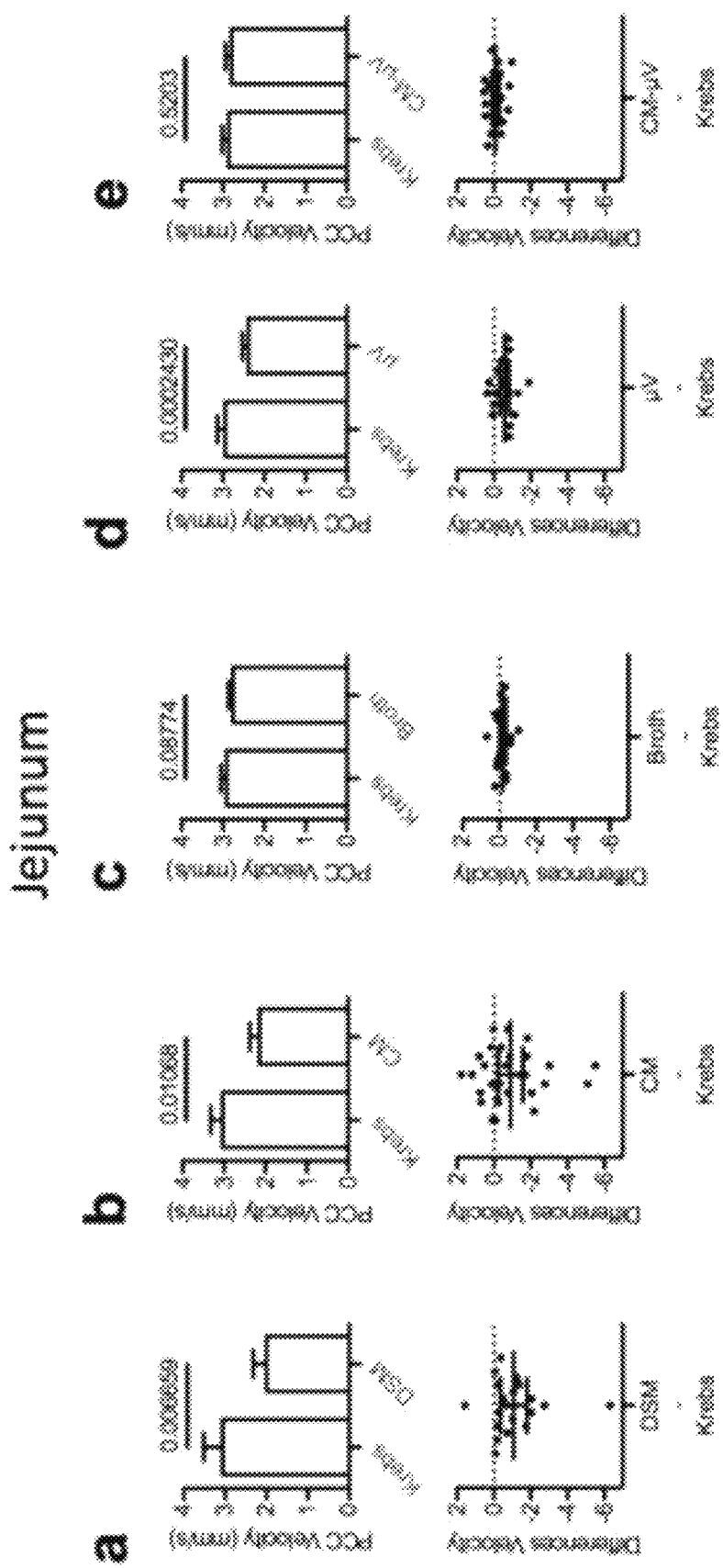
FIG. 2 illustrates the effects of adding *L. reuteri* DSM 17938 (DSM) in FIG. 2A, conditioned medium (CM) in FIG. 2B, culture medium (broth) in FIG. 2C, DSM derived microvesicles (μV) in FIG. 2D or conditioned medium minus microvesicles (CM-μV) in FIG. 2E on propagated contractile complex (PCC) velocity for mouse jejunal segments, in vitro. Upper panels: bar graphs showing means and standard errors. P values derived from paired t-tests are given above horizontal bars. Lower panels: individual value plots of difference (treatment-control Krebs) with 95% confidence intervals for each matching graph in upper row.

*L. reuteri* DSM 17938, CM, and MV all reduced PCC velocity to a similar degree in the jejunum. *L. reuteri* DSM 17938 significantly reduced jejunal PCC velocity by 34% when applied intraluminally (p=0.0067, n=20) (FIG. 2A). The CM recapitulated the effect of the parent bacteria and decreased PCC velocity by 29% (p=0.0107, n=28) (FIG. 2B). As a negative control, the broth used as media to culture the bacteria was tested independently and had negligible effect on jejunal PCC velocity (5% decrease) compared to Krebs control (p=0.0877, n=20) (FIG. 2C). Microvesicles isolated from the 72 hr culture significantly decreased jejunal PCC velocity by 19% (p=0.0002, n=20) (FIG. 2D). The CM-MV did not change jejunal PCC velocity when applied to the lumen (p=0.5203, n=20) (FIG. 2E).

Jejunal PCC Frequency

Figure 3:
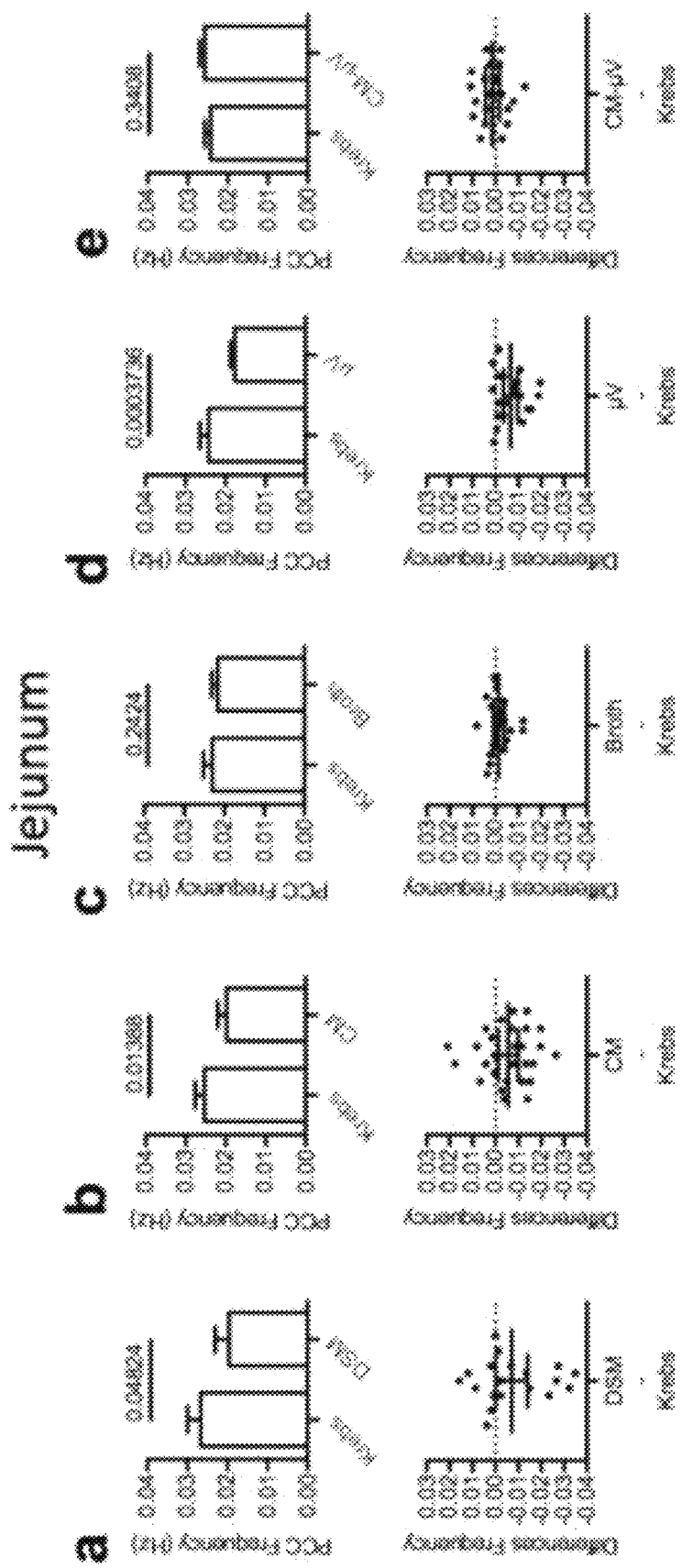
FIGS. 3 to 7 show the same relationships between upper and lower panels.

Decreases in PCC frequency in the jejunum were also produced by *L. reuteri* DSM 17938, CM, and MV. *L. reuteri* DSM 17938 significantly reduced PCC frequency by 26% in the jejunum (p=0.0482, n=20) (FIG. 3A). Similarly, CM decreased PCC frequency by 21% (p=0.0139, n=28) (FIG. 3B). The broth did not significantly change jejunal PCC frequency (6% decrease) when applied to the lumen (p=0.2424, n=20) (FIG. 3C). Microvesicles significantly decreased jejunal PCC frequency by 26% as comparable to the bacteria (p=0.0004, n=20) (FIG. 3D). Jejunal PCC frequency was not significantly affected by the luminal addition of CM-MV (p=0.3408, n=20) (FIG. 3E).

Jejunal PCC Amplitude

Figure 4:
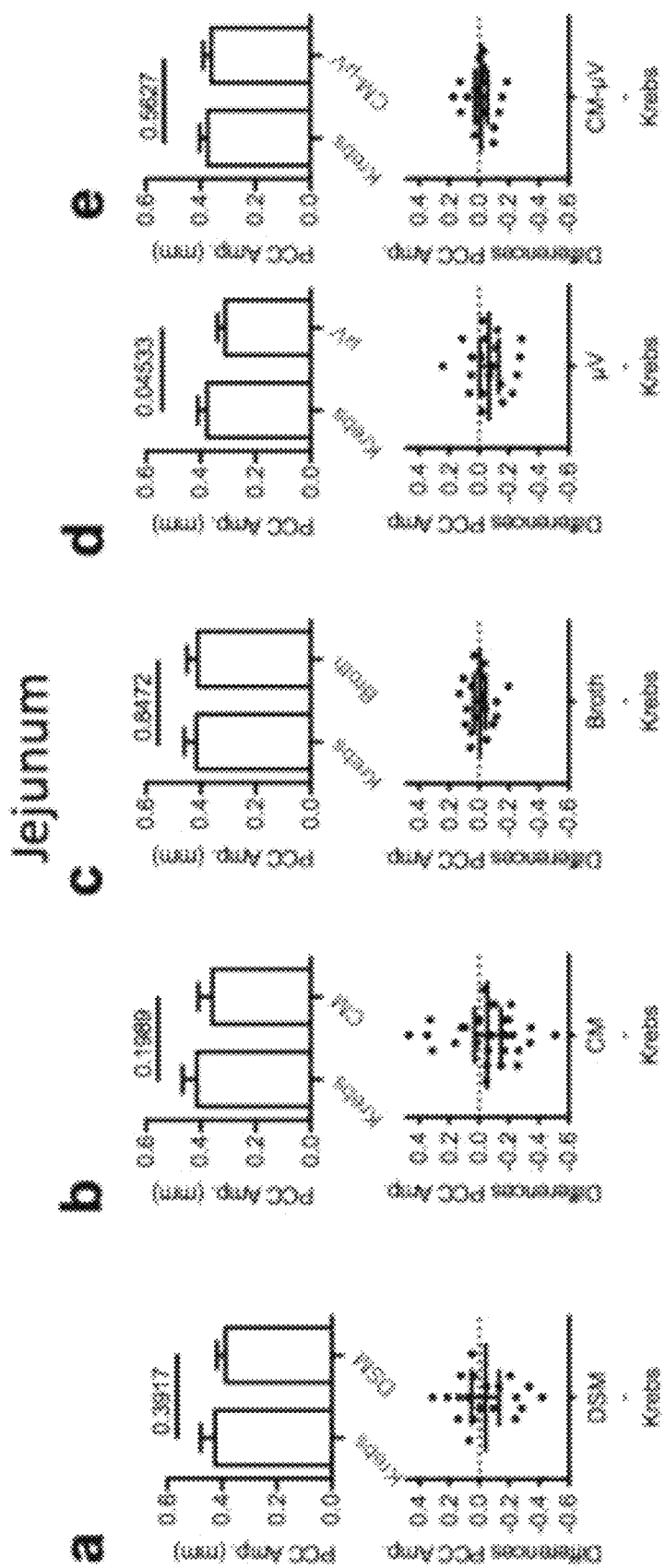

PCC amplitude in the jejunum was not significantly altered in any of the treatment groups, with the exception of the microvesicles. Microvesicles decreased jejunal PCC amplitude by 17% (p=0.0453, n=20) (FIG. 4D), despite this effect not being present in the *L. reuteri* DSM 17938 or CM trials (p=0.3917, n=20 and p=0.1989, n=28, respectively, FIGS. 4A and 4B). Broth and CM-MV did not change jejunal PCC amplitude (p=0.8472 and p=0.5627, n=20) (FIGS. 4C and 4E).

*L. reuteri* DSM-17938 and its Products Increased Colonic Motility Parameters

Colonic PCC Velocity

Figure 5:
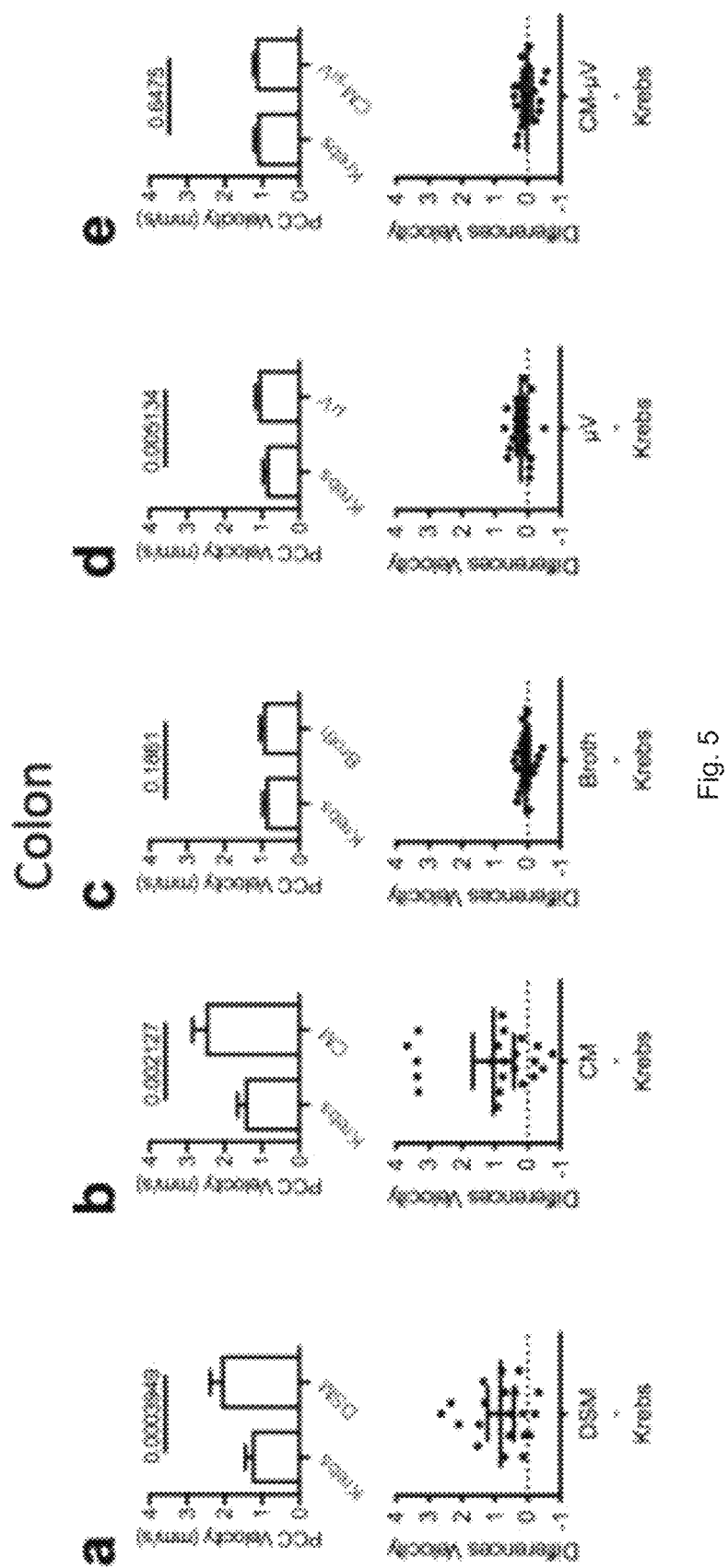

Colonic contractile motility was stimulated by the addition of either *L. reuteri* DSM 17938, CM, or MV. *L. reuteri* DSM 17938 significantly increased the velocity of PCC contractions in the colon by 65% (p=0.0004, n=20) (FIG. 5A). This was recapitulated by the CM, which significantly increased PCC velocity by 72% in the colon (p=0.0021, n=28) (FIG. 5B). Broth continued to have little effect on intestinal motility, increasing colonic PCC velocity by 8%, but not within the 0.05 significance range (p=0.1861, n=20)

(FIG. 5C). Microvesicles significantly increased the velocity of PCCs in the colon by 24% (p=0.0051, n=20), but to a lesser degree than that produced by *L. reuteri* DSM 17938 and CM (FIG. 5D). CM-MV applied intraluminally failed to change colonic PCC velocity significantly (p=0.6475, n=20) (FIG. 5E).

Colonic PCC Frequency

Figure 6:
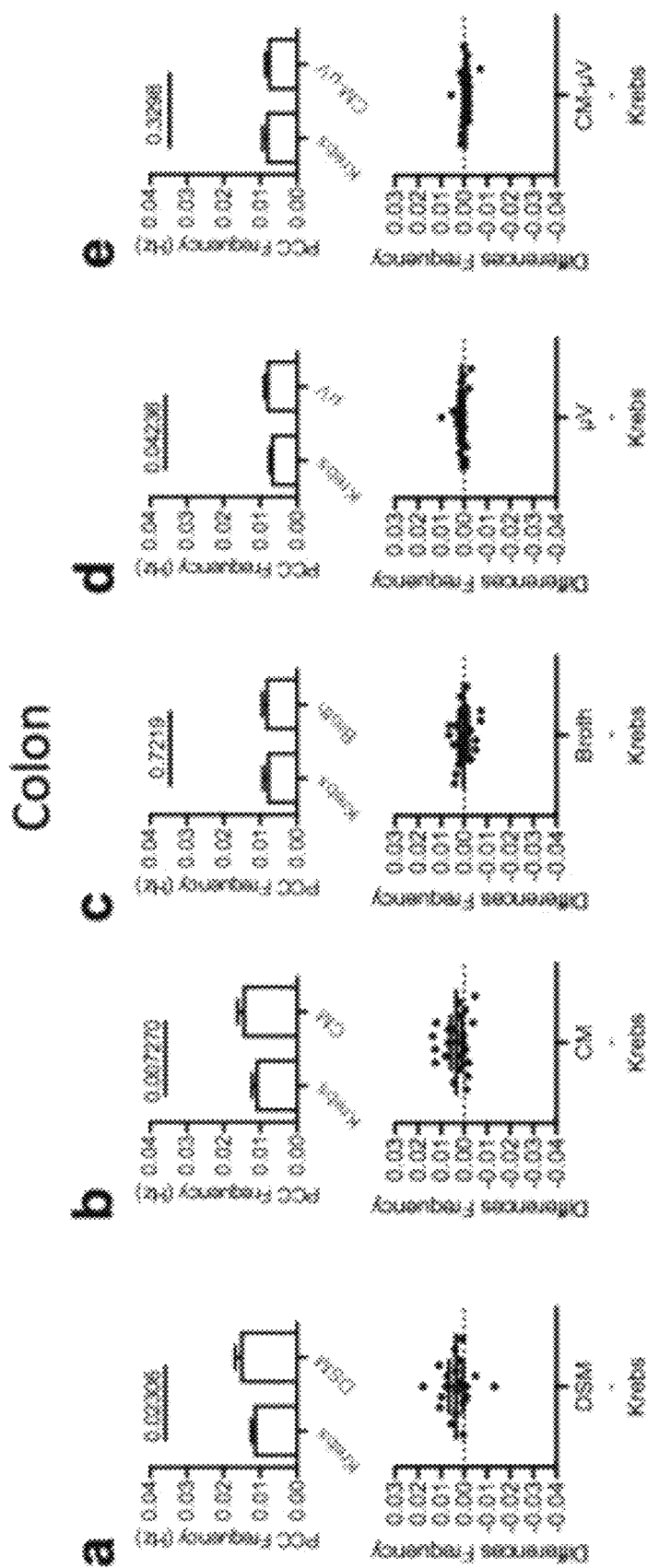
Figure 7:
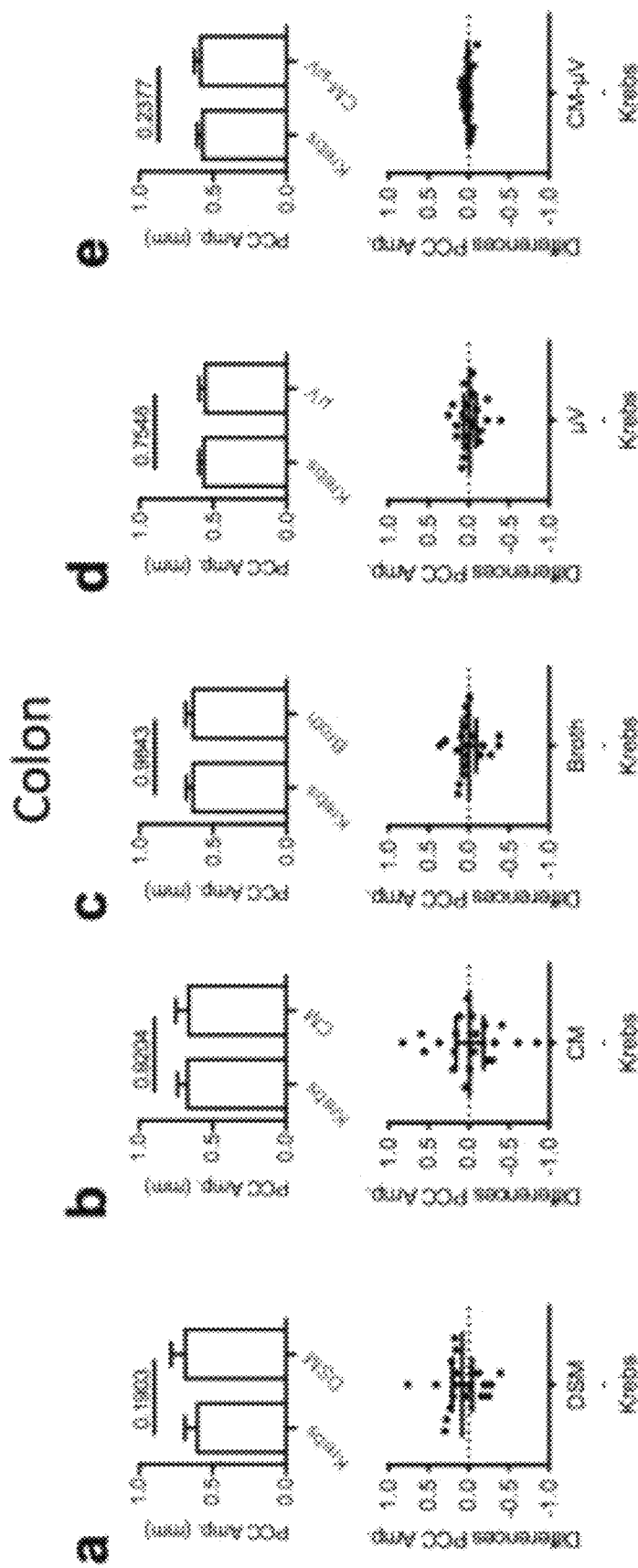

*L. reuteri* DSM 17938, CM, and MV all stimulated colonic motility by increasing the frequency of PCC contractions. *L. reuteri* DSM 17938 significantly increased colonic PCC frequency by 30% (p=0.0231, n=20) (FIG. 6A). In the same capacity, CM significantly increased PCC frequency by 31% in the colon (p=0.0073, n=28) (FIG. 6B). The broth increased colonic PCC frequency by as little as 4%, but not significantly (p=0.7219, n=20) (FIG. 6C). Similar to what was seen with PCC velocity, microvesicles increased the frequency of colonic PCCs by 18% (p=0.0424, n=20); (FIG. 6D). CM-MV did not significantly affect PCC frequency in the colon (p=0.3298, n=20) (FIG. 6E).

Colonic PCC Amplitude

PCC amplitude in the colon was not significantly affected by *L. reuteri* DSM 17938 or any of the other treatment groups (FIGS. 7A-E).

Conclusion

*L. reuteri* DSM 17938 had regional-specific effects on intestinal motility; decreasing jejunal and increasing colonic PCC velocity and frequency of contractions. The present study demonstrates that both the microvesicles and the conditioned media recapitulate the effect of *L. reuteri* DSM 17938 on intestinal motility in both the small intestine and the colon. Furthermore, these results were not seen when the conditioned media was applied following the removal of the microvesicles (CM-MV). All results have been summarized in FIG. 8.

These results demonstrate the role of microvesicles in *Lactobacillus* probiotic signaling with the host organism and their mechanism of action within the microbiome-gut-brain axis. This shows that the microvesicles produced by or shed by the bacteria are responsible for changes in gut motility induced by *L. reuteri* DSM 17938

Example 4—Isolated Bacterial Microvesicles Recapitulate the Effect of Bacteria on Pain Signaling The effect of microvesicles isolated from *L. reuteri* DSM 17938 culture medium on pain signaling was tested using TrpV1 expressing Jurkat cells in the presence of 10 µM capsaicin.

Materials and Methods

Cell Culture

Jurkat cells (Clone E6-1 (ATCC® TIB-152™), ATCC) were suspended in 2% fetal bovine serum (FBS) Roswell Park Memorial Institute (RPMI) medium at concentration ~5×10$^6$ cells/mL total volume of 20 mL.

*L. reuteri* DSM 17938 was cultured, harvested and stored as described in Example 3 above. The microvesicle isolation preparation from *L. reuteri* DSM 17938 was also done according to Example 3 above (48 h). Bacteria were diluted in MRS Broth to a final concentration of 10$^{10}$ CFU/ml, and kept frozen at −80° C. until used for experiments.

Ratiometric Calcium Flux Measured by Flow Cytometry

50 µg of each of two dyes, Fluo-3 AM (F1242; Sigma) and Fura Red AM (F3021; Sigma), were dissolved in 100 µL of 0.1% pluronic acid (PLURONIC® F127 dissolved in dimethyl sulfoxide (DMSO)). 50 µL of the Fluo-3 and 100 µL of the Fura Red solutions were then added to 20 mL of Jurkat cells, resulting in a ratio of Fluo-3 to Fura Red of 1:2.5. Cells were then incubated at 37° C. for 1 hr and washed with PBS (centrifugation at 300×g for 10 min). Cells were then resuspended in Dulbecco's Modified Eagle Medium (DMEM) or RPMI 1640 medium containing 2% of FBS.

At the day of the experiment, bacteria were thawed, washed in PBS three times, and then added to the cell cultures. Alternatively, microvesicles isolated from the bacteria (as described in Example 3) were thawed, washed and added to the cell cultures. Incubation was continued at 37° C. for an additional hour. The cell suspension was then spun down as above and resuspended in PBS containing 1.25 mM Ca$^{2+}$.

All experiments were performed on an BD FACSCelesta (BD Bioscience, Mississauga, Canada) equipped with the following lasers: Blue laser emitting at 488 nm, Red laser emitting at 640 nm and Violet laser emitting at 406 nm. Calibration was performed using BD PMT Beads (BD, Mississauga, Canada). Compensations were run with single colored BD compensations beads.

For the FACS experiment, one mL of the cell suspension was transferred to a 5 mL tube with a cell-strainer cap (Falcon 352235), and spun for 1 min prior to analysis. Capsaicin was prepared from a 100 mM stock solution, and diluted to 100 µM in PBS containing calcium and magnesium.

Background corresponding to non-specific calcium flux was recorded for 30 seconds. All samples were acquired for a fixed time (30 or 60 second) with a constant flow rate (number of cells/second). 100 µl of the Capsaicin solution (resulting in a final concentration of 10 µM) was added to the cell suspension immediately before recording by FACSCelesta.

Recording was continuous at a rate of 400-600 events/second for 30 to 60 seconds in total.

Both Fluo-3 and Fura Red were excited at 488 nm with Fluo-3 emission detected at 575 nm and Fura Red emission detected at 610 nm. Data were collected in histograms displaying the ratio of violet to blue Fluo-3 fluorescence vs. time and Fura Red fluorescence vs. time.

Ratiometric analysis of Fluo-3/Fura Red was measured by excitation by the Blue laser (488 nm). Emission was detected by two different filter sets: increases in emission were monitored off the Violet laser (610/20 nm), while a decrease in emission was detected off the Blue laser (575/25 nm). The ratiometric, 'Fluo-3/Fura Red Ratio' was calculated as the increasing signal stimulated by the Violet laser over the decreasing signal stimulated by the Blue laser (406 nm/488 nm) using the Kinetics tool in FlowJo software (Tree Star Inc., OR, USA).

Results

Figure 9:
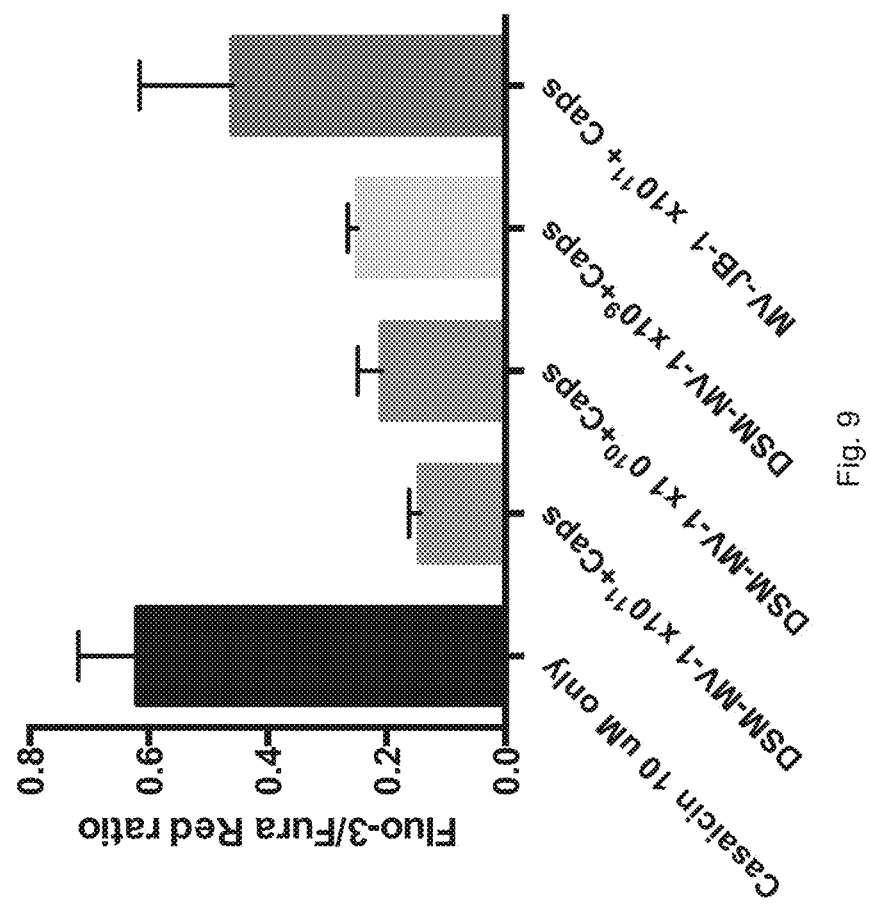
FIG. 9 illustrates the effect of microvesicles on TrpV1 signaling. The graph illustrates the capsaicin-induced response obtained using microvesicles isolated from *L. reuteri* DSM 17938 (DSM-MV) and microvesicles isolated from the *Lactobacillus rhamnosus* JB-1 bacterial strain (MV-JB-1).

Capsaicin on its own or MVs isolated from another bacterial strain, JB-1, (MV-JB-1) were used as control. The readout (FIG. 9) for capsaicin activation was calcium entry into the Jurkat cells, which increased the ratio of FLuo-3/Fura Red ratio. Capsaicin on its own at 10 µM induced calcium entry into the Jurkat cells, a response which was significantly blocked by using MVs isolated from *L. reuteri* DSM 17938 (DSM-MV) at a high concentration corresponding to *L. reuteri* DSM 17938 at 10$^{11}$ CFU/mL. Lower concentrations of *L. reuteri* DSM 17938 MVs corresponding to *L. reuteri* DSM 17938 at 10$^9$-10$^{10}$ CFU/mL had a similar, but slightly reduced effect, whereas MVs from *L. rhamnosus* JB-1 at a high concentration corresponding to JB-1 at 10$^{11}$ CFU/mL did not have a significant effect on the response to capsaicin treatment.

Example 5—the Onset of the Effect on Spinal
Nerve Firing with Isolated Bacterial Microvesicles
is Faster Compared to the Onset of the Effect
Obtained with Whole Bacteria The inventors herein surprisingly observed that microvesicles from Lactobacillus reuteri DSM 17938 did not only recapitulate the effect of whole bacteria on mesenteric nerve firing, but that MVs were able to produce an enhanced effect compared to whole bacteria. This finding was obtained by analyzing the amount of time it takes from treatment initiation to the peak response (onset of full effect) when using isolated L. reuteri DSM17938 microvesicles compared to using whole bacteria.

Materials and Methods

L. reuteri DSM 17938 were grown, harvested and stored as described in Example 3 above. The microvesicle isolation and preparation from L. reuteri DSM 17938 were done according to Example 3 above.

Jejunal mesenteric nerve recordings were performed as described previously (Perez-Burgos et al. (2013); Perez-Burgos et al. (2015)). In short, a 3 cm segment of mouse jejunum was excised and mounted on an agar-coated petri dish filled with oxygenated Krebs buffer and an L-type calcium channel blocker, nicardipine (3 µM). The luminal contents of the jejunum were flushed with Krebs and the oral and anal ends were cannulated with silicon tubing to allow the flow of treatments through the jejunal segment. The mesenteric nerve bundle was carefully isolated from the jejunal segment by gently scraping away the attached mesentery with fine forceps. The dish containing the nerve preparation was then mounted on the microscope stage and perfused continuously using a pump with warm, oxygenated Krebs.

The exposed nerve bundle was sucked onto with a glass micropipette attached to a patch-clamp electrode holder. Multi-unit electrical activity was recorded from the nerve bundle using a Multi-Clamp 700B amplifier and Digidata 1440A signal converter. Control periods were recorded for 15-30 min during luminal Krebs perfusion. Luminal L. reuteri DSM 17938 or microvesicles were applied immediately following the control for a duration of 20-30 min.

Multi-unit electrical activity was analyzed for single-unit activity using principle component analysis (PCA) and spike waveform analysis in the Dataview program (Heitler (2007)). The time to peak response was measured from the time the treatment was initiated to the time when the response was seen (change in firing rate).

Results

Figure 10:
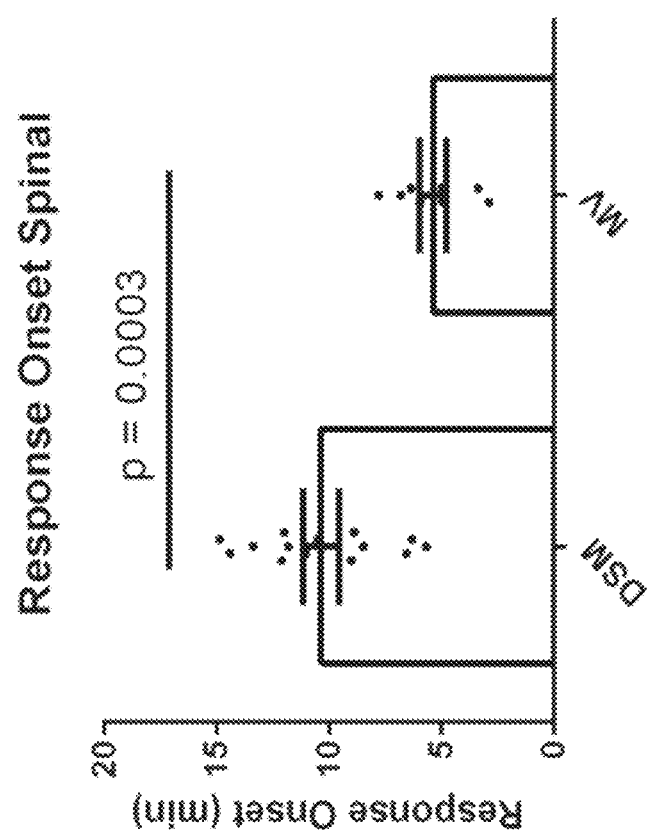
FIG. 10 is a graph illustrating the timing of the onset of a response in a mesenteric nerve firing model using *L. reuteri* DSM 17938 (DSM) and microvesicles isolated from *L. reuteri* DSM 17938 (MV).

L. reuteri MVs (MV) were able to initiate a nerve firing response quicker, leading to an earlier onset of the effect, compared to the whole bacteria (DSM) as shown in FIG. 10.

Example 6—Culture and Isolation Protocol

A typical workflow of MV preparation comprises following steps: cultivation, removal of intact bacteria and MV isolation from the culture filtrate, and optionally the pre-concentration and purification. The selection of particular methods relies on many factors, e.g., the amount of material to be processed and the required purity according to subsequent applications.

Culturing Conditions

The inventors identified culturing parameters for bacterial strains resulting in the production of therapeutic MVs with an improved effect in preferred models of gastrointestinal motility and gastrointestinal pain. L. reuteri DSM 17938 was cultured under normal culturing conditions, i.e., anaerobically cultured in de Man-Rogosa-Sharpe (MRS) medium at 37° C. for 24 h in a bottle/flask, with the addition of 2% sucrose as inducing factor.

Isolation Conditions

Preparation of bacterial MVs included the above described defined steps of culturing the bacteria followed by MV isolation. To obtain MV fractions of high numbers, high purity, and with retained biological effect, the bacterial supernatant was centrifuged at 4 000 rpm for 20 minutes (Beckman high speed centrifuge with JA-18 fixed-angle rotor), followed by centrifugation for a second time at 10 000×g for 20 minutes and then filtered through a 0.45 µm filter. These first steps removed live bacteria and large debris. The pellet was then discarded and the supernatant containing the MVs was loaded onto a sucrose cushion and ultra-centrifuged at 118000×g at 4° C. for 20.5 hours. Finally, the pellet was washed and centrifuged at 118 000×g, at 4° C. overnight to get the therapeutic MVs as a pellet.

Example 7—Immune Stimulation by Lactobacillus
reuteri DSM 17938 Derived Microvesicles (MVs)

In this Example, it has been shown that MVs derived from the cell free supernatant (CFS) of Lactobacillus reuteri DSM 17938 had an immune stimulatory and interferon gamma (IFN-γ) dampening activity, showing that gut bacteria-derived extracellular MVs can be important modulators of human immunity.

Material and Methods

Ethical Statement and Isolation of Peripheral Blood Mononuclear Cells

Healthy, anonymous, adult volunteers (age 18-65) were included in this study, which was approved by the Regional Ethic's Committee at the Karolinska Institute, Stockholm, Sweden {Dnr 04-106/1 and 2014/2052-32}. All study subjects gave their informed written consent. Venous blood was collected in heparinized vacutainer tubes (BD Biosciences Pharmingen) and diluted with RPMI-1640 cell culture medium supplemented with 20 mM HEPES (HyClone Laboratories, Inc.). Peripheral blood mononuclear cells (PBMC) were then isolated by Ficoll-Hypaque (GE Healthcare Bio-Sciences AB) gradient separation. The PBMC were washed in RPMI-1640, resuspended in freezing medium containing RPMI-1640 40%, fetal calf serum 50% and DMSO 10%, gradually frozen in a freezing container (Mr Frosty, Nalgene Cryo 1° C.; Nalge Co.) and stored in liquid nitrogen.

In Vitro Stimulation of PBMC

PBMC were thawed, washed and viability assessed by Trypan blue staining followed by counting with a 40× light microscope. Cells were re-suspended in cell culture medium (RPMI-1640 supplemented with HEPES (20 mM), penicillin (100 U/ml), streptomycin (100 µg/ml), L-glutamine (2 mM) (all from HyClone Laboratories, Inc.) and fetal calf serum 10% (Gibco by Life Technologies)) at a final concentration of $1\times10^6$ cells/ml. Cells were seeded in flat-bottomed cell culture plates and incubated at 37° C. with 5% $CO_2$ atmosphere. Staphylococcus aureus cell free supernatant (CFS) was used as stimuli at 2.5% (v/v), and isolated MVs from Lactobacillus reuteri DSM 17938 were added to PBMC at a MV-to-cell ratio of 500:1, 100:1 and 20:1.

Isolation of Microvesicles

Lactobacillus reuteri DSM 17938 bacterial cells were grown in de Man Rogosa Sharpe medium (Oxoid) for 24 h at 37° C. The bacteria cells were removed from the culture broth by centrifugation at 5,000×g for 10 min at 4° C. and followed by another centrifugation at 10,000×g for 10 min at 4° C. Then, the supernatants were filtrated using 0.45 μm pore filter (Millipore). Cell free supernatants were concentrated using Amicon Ultra filter unit with a MwCO of 100 kDa, which remove proteins and other molecules under 100 kDa. The supernatants were loaded on top of 12% sucrose cushion with 50 mM Tris buffer pH 7.2, with the volume ratio 5:1, and centrifuged by Beckman coulter Optima L-80XP. ultracentrifuge (Beckman coulter, United States) at 118,000×g at 4° C. for 3 h. The supernatants were discarded, resuspended the pellet in PBS buffer and ultra-centrifuged for the second time (118,000×g at 4° C. for 3 h). The pellets were then dissolved in PBS, aliquoted and stored at −70° C.

Experimental Procedure

The isolated MVs from the *Lactobacillus reuteri* DSM 17938 were added to PBMC at a MV-to-cell ratio of 500:1, 100:1 and 20:1 and incubated for 48 h. The cell culture supernatants were collected and analyzed for induction of cytokines using ELISA.

ELISA

Secreted levels of the cytokines IL-1ra (R&D Systems-BioTechne), IL-1β, IL-6, IL-10, IL-17A and IFN-γ (MabTech AB) were measured in cell culture supernatants using sandwich ELISA kits according to the manufacturer's instructions. Absorbance was measured at a wavelength of 405 nm using a micro-plate reader (Molecular Devices Corp.) and results analyzed using SoftMax Pro 5.2 rev C (Molecular Devices Corp.).

Statistics

All statistical tests were done using GraphPad Prism (GraphPad Software). All data was considered non-parametric whereby Dunn's multiple comparison or Mann-Whitney t-tests were employed. Differences were considered significant when $p<0.05$ and the following significance levels were used *$p<0.05$; **$p<0.01$.

Results

Figure 11:
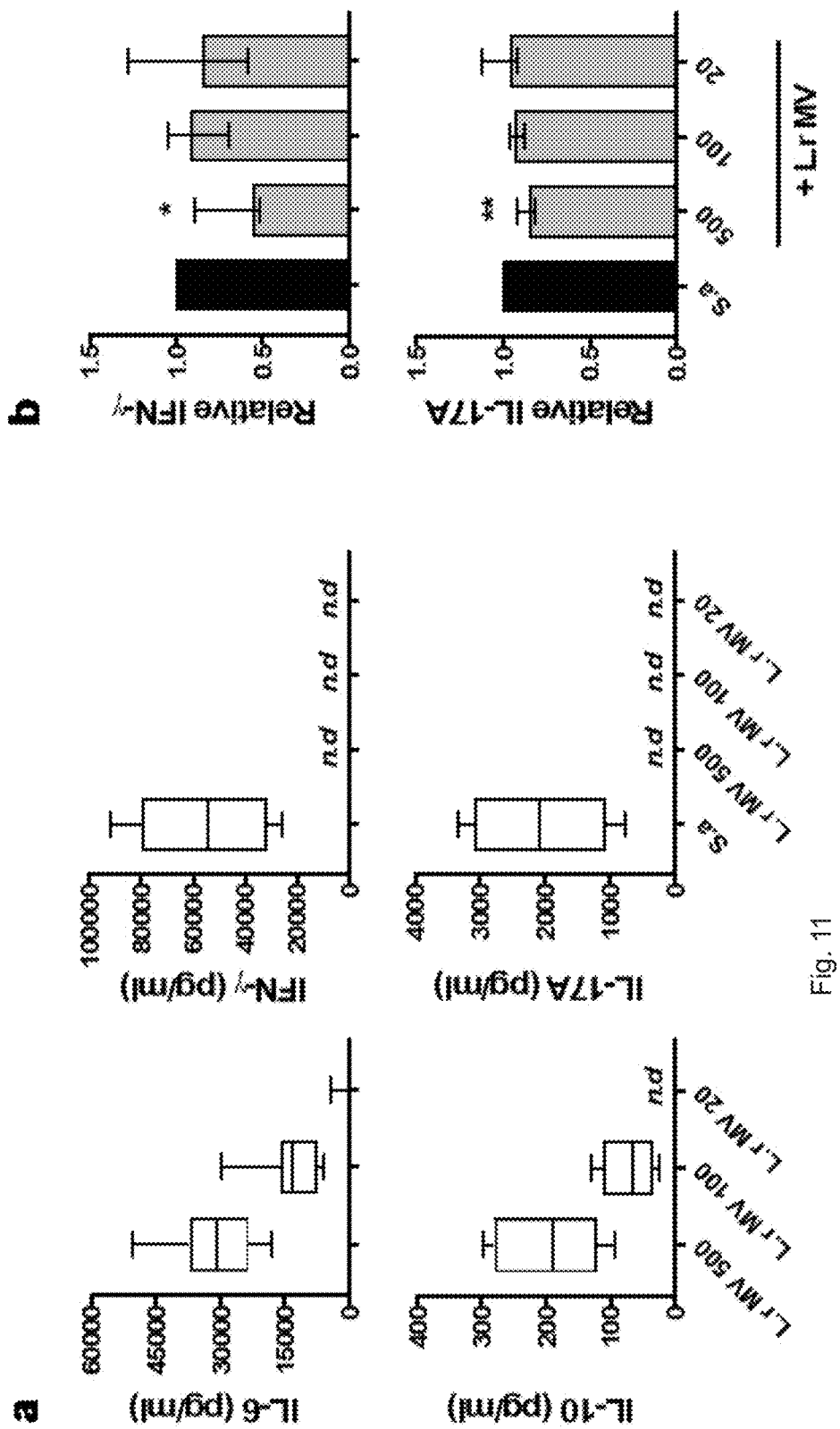
FIG. 11 illustrates that *L. reuteri* DSM 17938-derived microvesicles (MVs) are immune modulatory and dampen IFN-γ and IL-17A responses. Evaluation of the immunomodulatory effects of purified *L. reuteri* DSM 17938-derived MV s in PBMC cultures.

*Lactobacillus reuteri* DSM 17938 MVs clearly induced the production of both IL-6 and IL-10 in a concentration dependent manner, while no induction of IFN-γ or IL-17A was detected (FIG. 11A). Moreover, adding isolated MVs to *S. aureus*-stimulated PBMC significantly dampened IFN-γ and IL-17A secretion to a similar extent as the high MV fraction (FIG. 11B).

Example 8 —*Lactobacillus reuteri* Derived Microvesicles (MVs) Protect Epithelial Barrier Integrity from the Detrimental Effect of Enterotoxigenic *Escherichia coli*

Material and Methods

Isolation of Extracellular Microvesicles (MVs)

*Lactobacillus reuteri* DSM 17938 bacterial cells were grown in Man-Rogosa-Sharpe medium, harvested after 24 h and removed from the culture broth by centrifuging at 5,000×g for 10 min at 4° C. and followed by centrifuge at 10,000×g for 10 min at 4° C., after which any residual cells were removed from the supernatant by filtration using 0.45 μm pore filter. Supernatants were concentrated using Amicon Ultra filter (100 kDa), which remove proteins and other molecules under 100 kDa. The supernatants were centrifuged by Beckman coulter Optima L-80XP ultracentrifuge (Beckman coulter, United States) at 118,000×g at 4° C. for 3 h. The supernatants were discarded, the pellets were resuspended in PBS buffer and ultra-centrifuged for the second time (118,000×g at 4° C. for 3 h). The pellets were then dissolved in PBS, aliquot and stored at −70° C.

Intestinal Permeability In Vitro (Caco-2/HT29 Cell Co-Cultures)

Epithelial Cell Culture (Caco-2/HT29)

Caco-2 and HT29 cells were separately grown in tissue culture flasks in Dulbecco's Modified Eagle's Medium (DMEM) supplemented with 10% fetal bovine serum, 1% non-essential amino acids, and 1% penicillin and streptomycin, at 37° C. under an atmosphere of 5% $CO_2$ with 90% relative humidity. Caco-2 and HT29 cells were grown in 25 $cm^2$ tissue culture flasks and split at 80-90% confluence using 0.25% trypsin and 0.02% ethylenediaminetetraacetic acid (EDTA) solution. The cells were seeded at a density of $6\times10^4$ cells per 25-$cm^2$ flask.

Cell Co-Cultures

Caco-2 and HT29 cells were seeded on the apical chamber of Transwell inserts (Transwell-COL collagen-coated membrane filters) with 9:1 proportion and grown in 12-well Transwell plates with a final density of $1\times10^5$ cells/$cm^2$ in each insert. Cells were maintained in the same conditions and allowed to grow for 21 days with medium (0.5 ml in the apical side and 1.5 ml in the basolateral side) changes every other day to allow the cells to become differentiated.

Cell Layer Integrity

The integrity of the cell layer was determined using two methods: Transepithelial electrical resistance (TEER) and determination of fluorescein isothiocyanate-dextran (FITC-dextran) permeability.

The cell monolayer integrity during the experiments was determined by Transepithelial electrical resistance (TEER) measurement using the Millicell electrical resistance system (Millipore, Darmstadt, Germany). Three different areas were chosen to detect the TEER values in each well and the averages were the final results. TEER values above 250 $\Omega cm^2$ were used for the permeability studies.

Seeded Caco-2/HT29 cells were pre-treated with live *Lactobacillus reuteri* DSM 17938 cells at 100 multiplicity of bacteria (MOB) or extracellular microvesicles (MVs) from *Lactobacillus reuteri* DSM 17938 cells at 200 multiplicity of MV for 6 h before challenge with ETEC (pathogenic enterotoxigenic *E. coli*, known for having a disruptive effect on epithelial integrity) at 100 multiplicity of infection (MOI) for an additional of 6 h. TEER was measured prior to pre-treatment and challenge with ETEC, followed by measurement every second hour during the entire challenge. In order to quantify the paracellular permeability of monolayers, 1 mg/mL of 4 kDa fluorescein isothiocyanate-dextran (FITC-dextran; Sigma) was added to the apical side of the inserts at the start of the challenge with ETEC. Samples from the basolateral compartment were taken after 6 h of incubation. The diffused fluorescent tracer was then analyzed in triplicate by fluorometry (excitation, 485 nm; emission, 520 nm) using a FLUOstar Omega Microplate Reader (BMG Labtech, Ortenberg, Germany).

Results

The challenge with ETEC induced a reduction in TEER. Both *L. reuteri* derived MVs and bacteria cells were partly able to protect the epithelial monolayer from this challenge (FIG. 12). 6 h after ETEC challenge, the decline of TEER for the ETEC group reached 35%, and pre-treatment with the *L. reuteri* bacteria cells and MVs both showed significantly higher TEER as compared to ETEC treated group.

Figure 12:
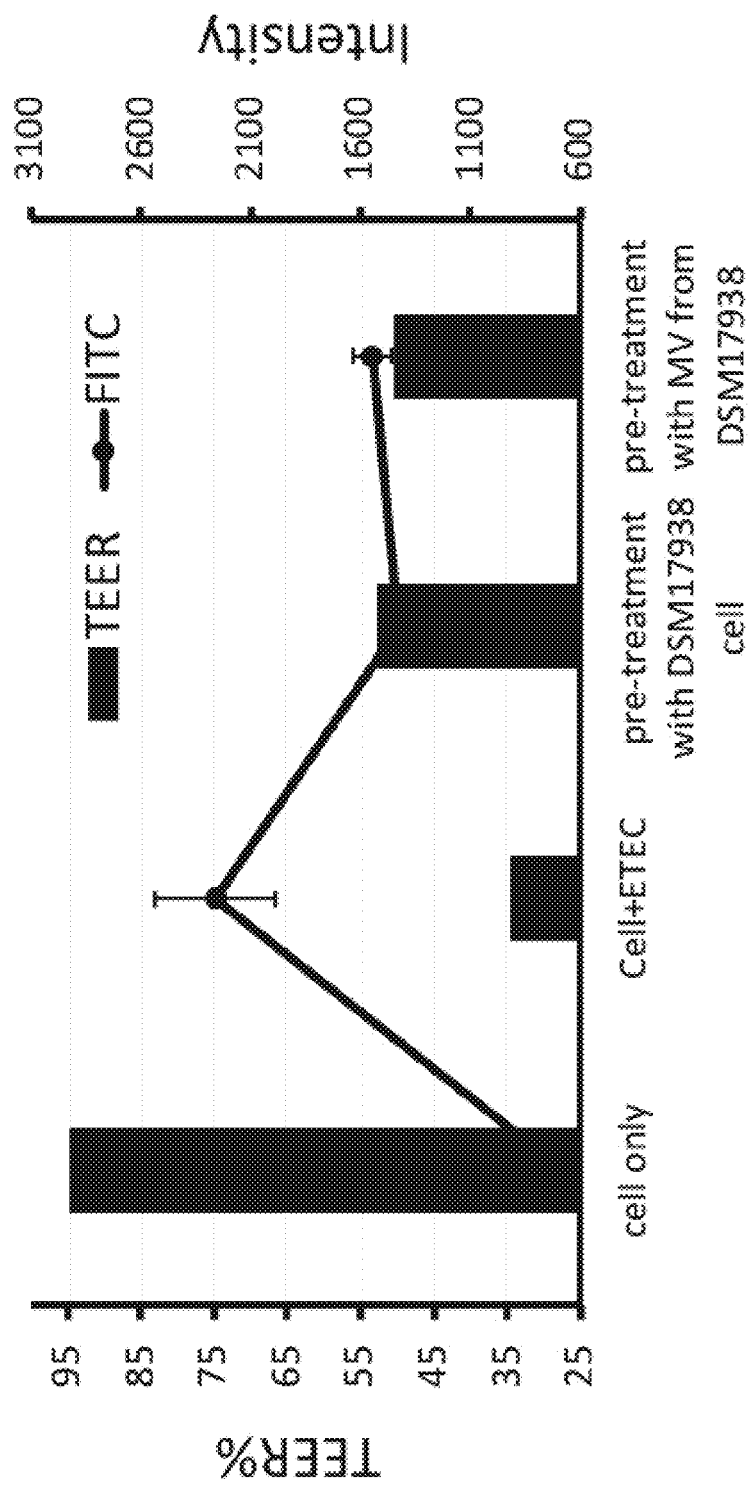
FIG. 12 illustrates that *L. reuteri* DSM 17938 and *L. reuteri* DSM 17938-derived microvesicles protected epithelial integrity from detrimental effects of enterotoxigenic *Escherichia coli* (ETEC).

The protective effect of *L. reuteri* derived MVs and bacteria cells against ETEC damage to the monolayer was also apparent in the FITC-dextran flux experiments (FIG. 12). Pre-treatment of the monolayers with *L. reuteri* derived MVs and bacteria cells decreased the leakage of FITC-dextran compared with the ETEC group.

Thus, both L. reuteri derived MVs and bacteria cells showed protection effect of the ETEC-induced damage to the Caco-2/HT29 co-cultures monolayers.

Example 9—Alteration in Enzymatic Activity Associated with MV Production

Lactobacillus reuteri DSM 17938 and Lactobacillus reuteri DSM 32846 was cultured and subjected to a number of inducing biotic treatments. The response, with regards to alterations in MV production, to these inducing treatments was determined using an enzymatic assay and compared to the response obtained for controls, i.e. bacterial cultures without inducing treatments. The enzymatic activity was then measured in the bacterial conditioned medium.

Materials and Methods

Culturing and Biotic Treatment

L. reuteri DSM 17938 or L. reuteri DSM 32846 were inoculated from frozen stock in 25 mL de Man-Rogosa-Sharpe (MRS) medium under normal culturing conditions, i.e., anaerobically cultured at 37° C. overnight. Then, the bacteria (40 mL) were re-inoculated in 400 mL SIM together with either supernatant (4%) from other bacterial cultures or by the addition of other bacterial cells (25%, washed and suspended in PBS) and then cultured for another 48 hours. The bacterial samples investigated are summarized in the table below.

TABLE 3 overview of bacterial samples and treatments

| MV producing bacterial strain | Biotic treatment |
| --- | --- |
| L. reuteri DSM 17938 | — (control) |
| L. reuteri DSM 17938 | 4% supernatant of Bifidobacterium longum ATCC BAA-999 |
| L. reuteri DSM 17938 | 4% supernatant of Bifidobacterium longum DSM 32947 |
| L. reuteri DSM 17938 | 4% supernatant of Lactobacillus paracasei LMG-P-17806 |
| L. reuteri DSM 17938 | 25% cells of Bifidobacterium longum DSM 32947 |
| L. reuteri DSM 32846 | — (control) |
| L. reuteri DSM 32846 | 4% supernatant of Bifidobacterium longum DSM 32947 |

Bifidobacterium longum ATCC BAA-999 and Lactobacillus paracasei LMG-P-17806 are commercially available bacterial strains and have been deposited at ATCC (American Type Culture Collection) and the Belgian Coordinated Collections of Microorganisms, Microbiology Laboratory, respectively.

The experimental setup relates to the probiotic bacterial strains and different biotic treatments and has been designed to mimic the true up-scaled situation in production settings, or to mimic the situation in the human gastrointestinal tract. The 4% supernatant of the biotic treatments during culturing were chosen as a relevant concentration of being enough to possibly have an effect on the one hand but on the other hand not adding too much due to the risk of having components from the inducing biotic bacteria as part of the end product. The higher concentration, 25%, of cells of the biotic treatment was selected to mimic the effect that would occur locally in the human gastrointestinal tract if the two (or more) bacterial strains were administered together as one combined composition.

Sampling

The bacterial samples were first centrifuged at 5000×g for 10 min, after which the supernatants were transferred to a new tube and then centrifuged for a second time at 10,000×g for 10 min to remove bacterial cells and bacterial cell debris. The supernatants, now containing the MVs, were filtered through a 0.45 μm filter, and kept on ice before further centrifuging using an ultracentrifuge at 32 000 rpm at 4° C. for 3 h (Beckman SW 32 Ti Rotor, Swinging bucket, 30 mL tubes). The supernatants were discarded (gently poured out, with help of a pipette). The MV containing pellets were carefully resuspended in resuspension media (phosphate buffered saline (PBS)) and again centrifuged at 32 000 rpm at 4° C., washing away the remnants of the cultivation media. The resuspension volume varied, between 100-300 μL, depending on the pellet size. The samples were aliquoted and stored at −70° C.

Enzymatic Activity

5'-nucleotidase enzyme activity was used as a measure to quantify alterations in numbers and/or potency of MVs produced by the different inducing biotic treatments. The samples obtained from the biotic inducing treatments above were thawed and then tested in a 5'-nucleotidase activity assay using the Crystal Chem 5'-Nucleotidase Assay Kit (Crystal Chem, Elk Grove Village, IL, USA). In short, the procedure was performed in two steps. Firstly, reagent 1 (CC1) containing AMP was added to the supernatant samples to convert AMP to adenosine by any 5'-nucleotidase enzyme present in the supernatant samples. Adenosine was further hydrolysed into inosine and hypoxanthine by components in reagent 1. In the second step, reagent 2 (CC2) was added to convert hypoxanthine into uric acid and hydrogen peroxide, which was used to generate a quinone dye that was measured kinetically at 550 nm in a spectrophotometer. The 5'-nucleotidase activity in the samples was determined by calculating the change in absorbance between 3 and 5 minutes and comparing with the value from a calibrator sample.

Results

Figure 13:
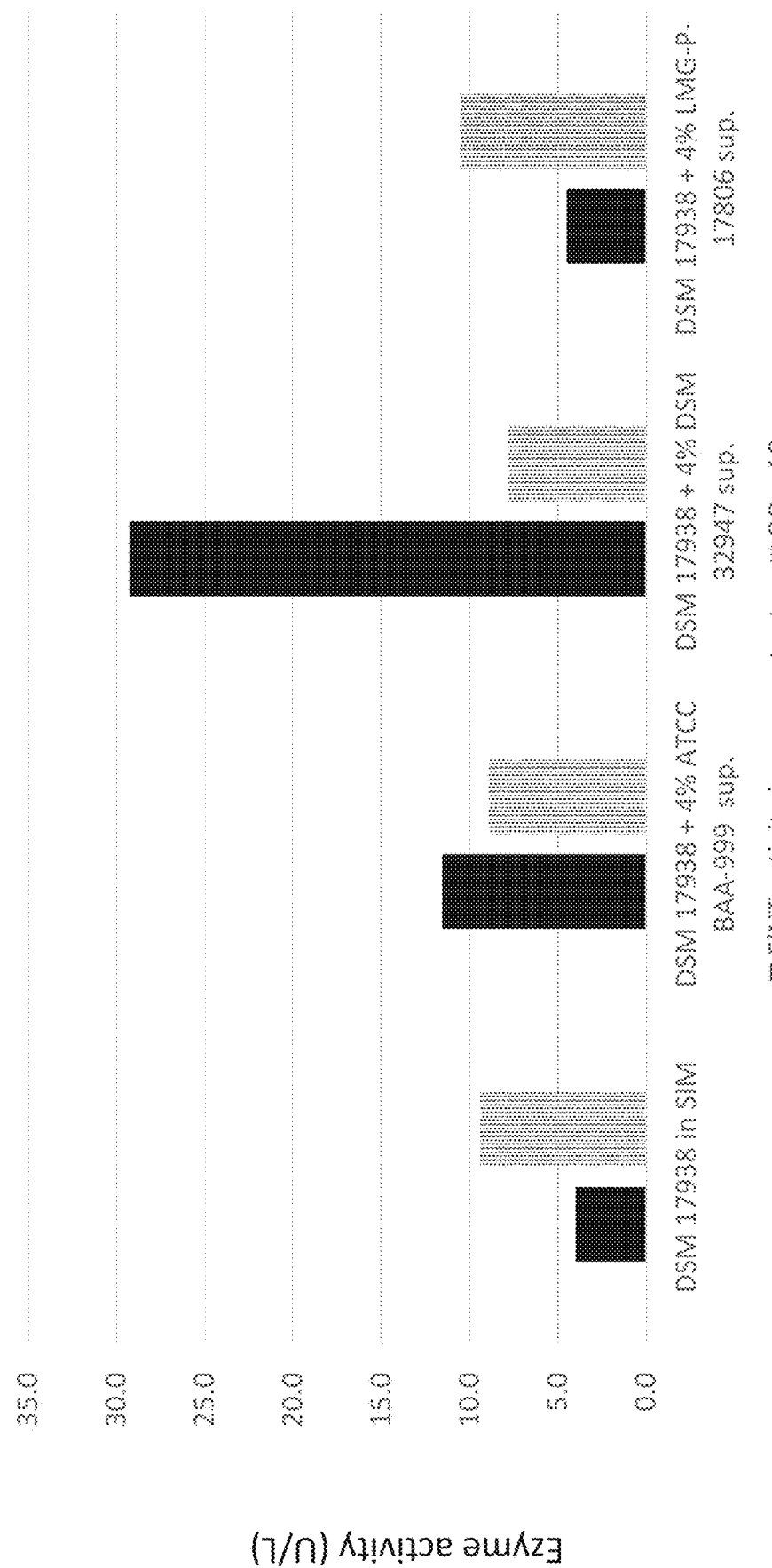
FIG. 13 illustrates 5'-nucleotidase activity in MV samples obtained from *L. reuteri* DSM 17938 (culturing *L. reuteri* DSM 17938 with an addition of 4% supernatant from *B. longum* ATCC BAA-999 or *B. longum* DSM 32947 in SIM media (DSM 17938+4% DSM 32947 sup. or DSM 17938+4% ATCC BAA-999 sup.) as compared to the *L. reuteri* DSM 17938 in SIM (control) or *L. reuteri* DSM 17938 with 4% supernatant from *L. paracasei* LMG-P-17806 (DSM 17938 in SIM or DSM 17938+4% LMG-P-17806 sup.)

FIG. 13 illustrates 5'-nucleotidase activity in MV samples obtained from L. reuteri DSM 17938 (for control and treated samples). As can be seen from the figure, the 5'-nucleotidase activity was increased in samples obtained from culturing L. reuteri DSM 17938 with an addition of 4% supernatant from B. longum ATCC BAA-999 or B. longum DSM 32947 in SIM media (DSM 17938+4% DSM 32947 sup. or DSM 17938+4% ATCC BAA-999 sup.) as compared to the L. reuteri DSM 17938 in SIM (control) or L. reuteri DSM 17938 with 4% supernatant from L. paracasei LMG-P-17806 (DSM 17938 in SIM or DSM 17938+4% LMG-P-17806 sup.) The effect of inducing biotic treatment on 5'-nucleotidase activity was most pronounced when L. reuteri DSM 17938 was cultured with supernatant from B. longum DSM 32947, but an effect was also obtained with supernatant from B. longum ATCC BAA-999. Optical Density (OD) scores from each sample illustrate that the relative cell count was not significantly altered between treatments.

Figure 14:
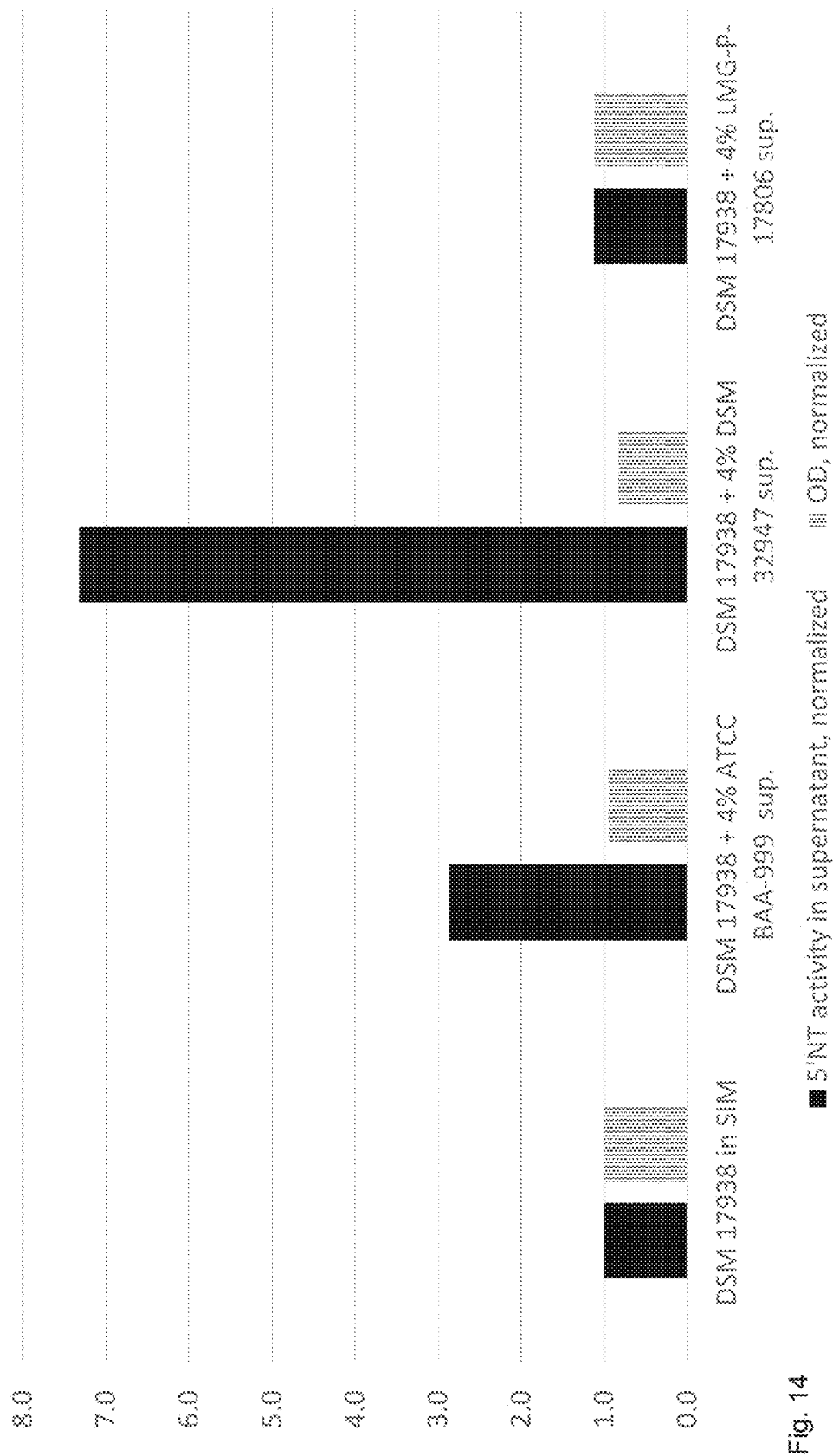
FIG. 14 shows the same results as those presented in FIG. 13 but which have been normalized in relation to the 5'-nucleotidase activity and optical density of DSM 17938 in SIM.

Results presented in FIG. 14 are the same as presented in FIG. 13 but have been normalized in relation to the 5'-nucleotidase activity and optical density of DSM 17938 in SIM, making it easy to compare the fold-change in 5'-nucleotidase activity in between different experiments.

Figure 15:
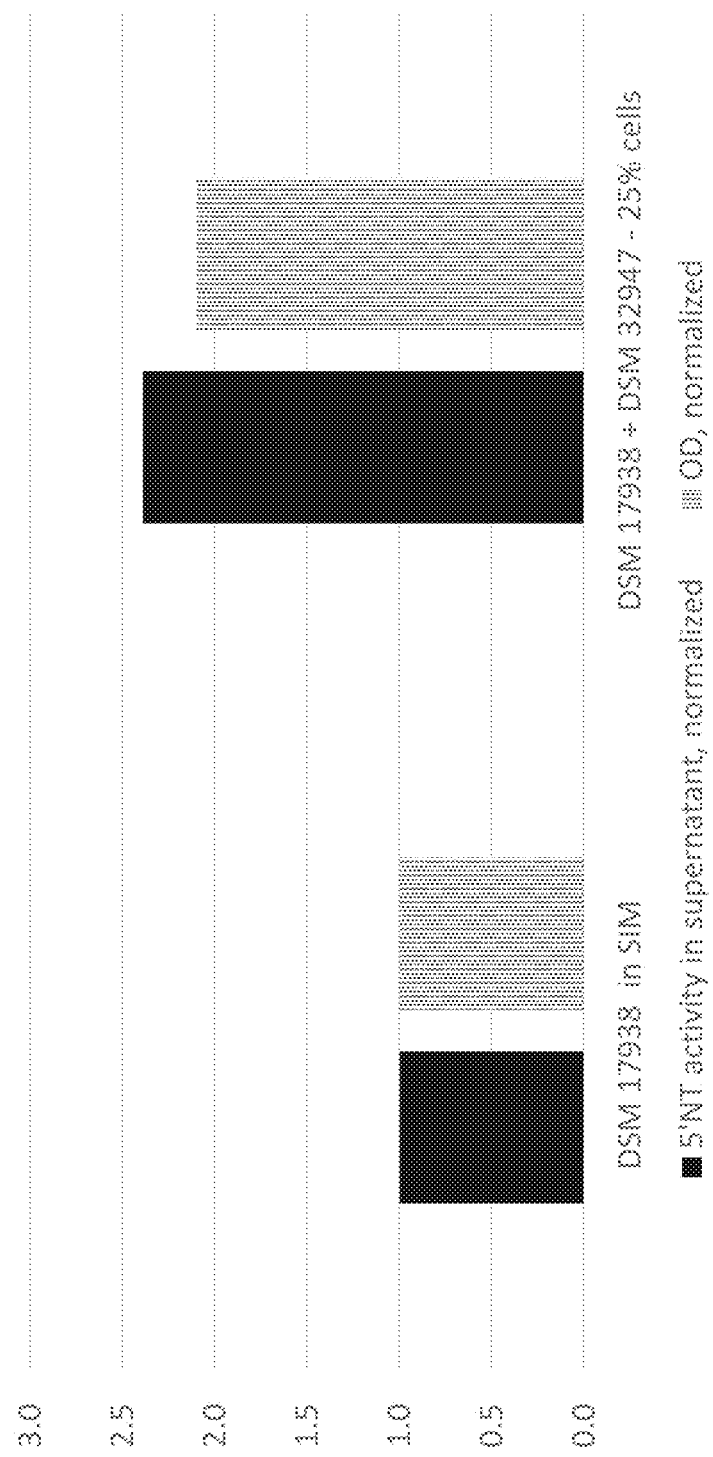
FIG. 15 illustrates the 5'-nucleotidase activity in control samples (DSM 17938 in SIM) as compared to samples obtained after inducing biotic treatment by co-culturing *L. reuteri* DSM 17938 with 25% cells from *B. longum* DSM 32947. The results have been normalized in relation to the 5'-nucleotidase activity and optical density of DSM 17938 in SIM.

The results in FIG. 15 (normalized), further illustrate that the 5'-nucleotidase activity was increased after inducing biotic treatment as compared to control samples (i.e., DSM 17938 in SIM) by co-culturing L. reuteri DSM 17938 with 25% cells from B. longum DSM 32947 in SIM media. OD scores from these samples illustrate the relative difference in cell numbers obtained by these different biotic treatments (i.e. an increased score in inducing biotic treatment samples because of a higher total number of bacterial cells).

Figure 16:
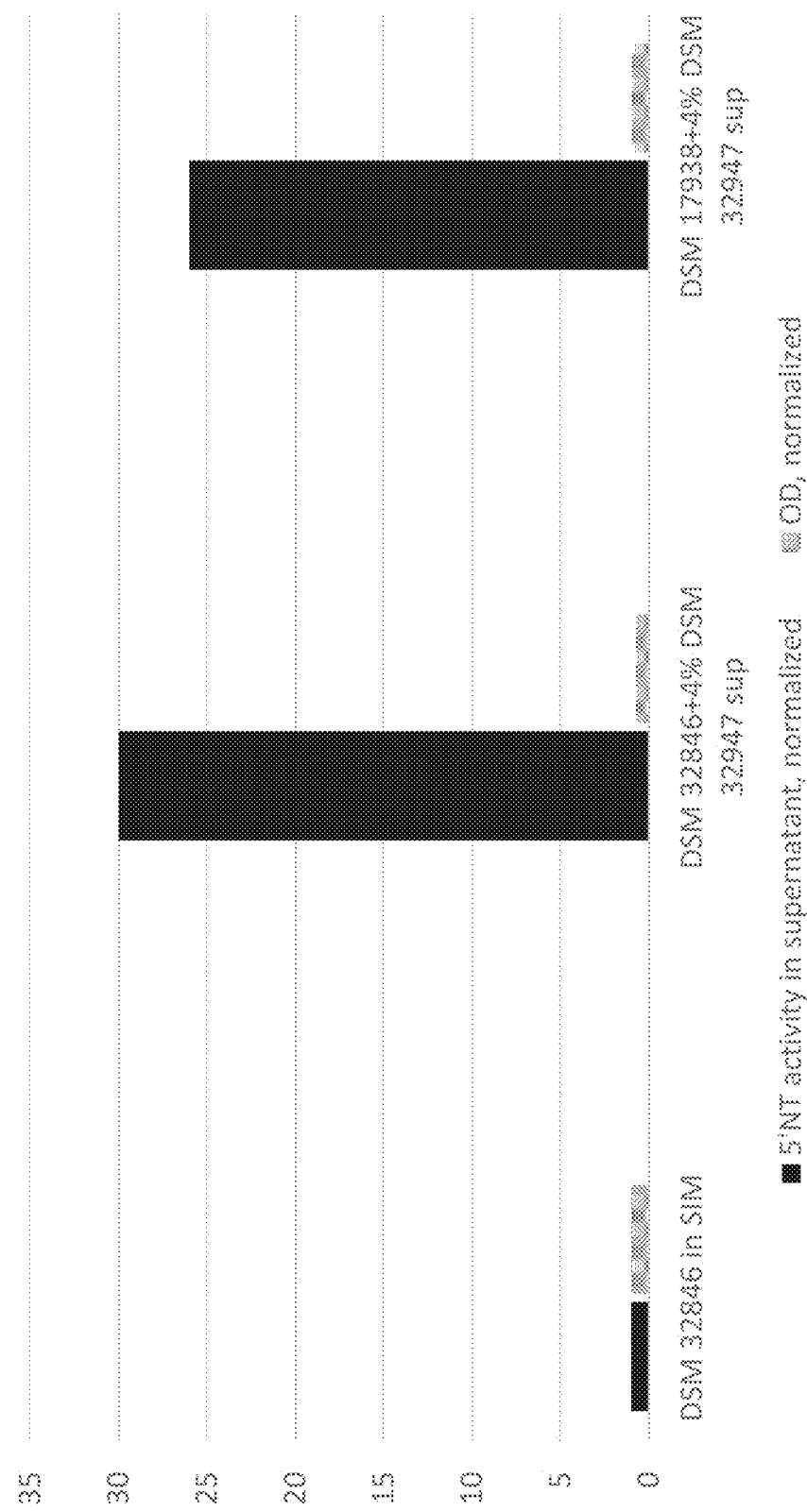
FIG. 16 illustrates the 5'-nucleotidase activity in MV samples after culturing *L. reuteri* DSM 32846 with 4% supernatant from *B. longum* DSM 32947 in SIM media (DSM 32846+4% DSM 32947 sup.) as compared to control *L. reuteri* DSM 32846 in SIM (DSM 32846 in SIM). The results have been normalized in relation to the 5'-nucleotidase activity and optical density of DSM 32846 in SIM.

FIG. 16 illustrates normalized values of the 5'-nucleotidase activity obtained in control and treated samples using *L. reuteri* DSM 32846. As can be seen from the graph, the enzymatic activity was increased by culturing *L. reuteri* DSM 32846 with an addition of 4% supernatant from *B. longum* DSM 32947 in SIM media (DSM 32846+4% DSM 32947 sup.) as compared to control *L. reuteri* DSM 32846 in SIM (DSM 32846 in SIM). OD scores from these samples illustrate the relative difference in cell numbers obtained by these different biotic treatments.

Example 10—Improved Antagonistic Effect by *Lactobacillus reuteri* DSM 17938 on TrpV1-Mediated Pain Signalling after Co-Culture with *Bifidobacterium longum* DSM 32947 or *Bifidobacterium longum* ATCC BAA-999

The effect of biotic treatments on the production of MVs by *Lactobacillus reuteri* DSM 17938 were tested in an in vitro Electric Field Stimulation (EFS) model using TrpV1-expressing neurons obtained from rat dorsal root ganglia (DRG) and the Cellectricon Cellaxess Elektra platform. *L. reuteri* DSM 17938 was cultured for 48 hours either as a control in simulated intestinal medium (DSM 17938 control SIM 48 h), or using an inducing biotic treatment consisting of co-culturing with 25% bacterial cells of either one of the two *Bifidobacterium longum* strains DSM 32947 or ATCC BAA-999 in SIM for 48 hours. (Recipe of SIM media can be found in Example 1). MVs were isolated from the different bacterial preparations according to Example 6. Primary rat DRG neuronal cultures were cultured for 48 hours in 384-well plates together with nerve growth factor (NGF) to mimic peripheral sensitization. The antagonistic effect of the obtained MV preparations on capsaicin-induced TrpV1 activation was then evaluated. On the day of the experiment, the DRG cultures were stained with a $Ca^{2+}$ indicator (Ca5; no wash screening kit) to enable imaging of calcium transients evoked by capsaicin, a specific TrpV1 agonist. First, the $EC_{50}$ of capsaicin was determined in separate EFS experiments, and this concentration was then added to all DRG cultures to induce TrpV1 activation. The effect of the MV preparations on TrpV1 activation was then evaluated in a dose-response format (six concentrations were tested in triplicate in each plate) with a starting concentration of 1:10 of the original MV stock concentration and using dilution steps of 1:3. The DRG cultures were incubated with the MV preparations for 1 hour prior running the EFS experiment. The plates were placed on the Cellaxess platform, and a series of EFS protocols were applied. These EFS protocols included pulse trains to capture changes in excitability that occur in the DRG cultures due to incubation with MV preparations. The effect of MV preparations on capsaicin-induced TrpV1 activation was then analysed and $EC_{50}$ values were determined for each of the preparations ($EC_{50}$ is generally described as the half maximal effective concentration and refers to the concentration of a substance which induces a response halfway between the baseline and maximum after a specified exposure time). Here ECK represents the 25% of stock concentration of MVs extracted from 400 ml liquid bacterial culture). The experiment was performed twice and a mean $EC_{50}$ value was calculated. The $EC_{50}$ value for the control experiment was 7.4, whereas the ECK values for both inducing biotic treatments were much lower (1.8 for DSM 17938+DSM 32947; 2.7 for DSM 17938+ATCC BAA-999). These results show that the inducing biotic treatments increase the antagonistic effect of the MV preparation on TrpV1 signalling, i.e., a lower amount of the induced MV preparations is required to inhibit the capsaicin induced TrpV1 signalling compared to the control MV preparation. An important aspect to mention here is that the control (DSM 17938 SIM 48h) has previously shown an inhibitory effect on TrpV1 signaling (see Example 4) and can therefore be considered to be a positive control. To summarize, by exposing the bacteria to inducing biotic treatments during culturing according to the invention, the bacteria were induced to produce therapeutic MVs. This in turn, improved the inhibitory/blocking effect on the capsaicin induced TrpV1 activation.

TABLE 4

Bacterial $EC_{50}$ value for TrpV1 inhibition

| Treatment | Bacterial $EC_{50}$ value for TrpV1 inhibition |
|---|---|
| Control: DSM 17938 SIM 48 h | 7.4 |
| Inducing treatment 1: DSM 17938 + DSM 32947 48 h | 1.8 |
| Inducing treatment 2: DSM 17938 + ATCC BAA-999 48 h | 2.7 |

The $EC_{50}$ values are presented as the % of stock concentration of MVs extracted from 400 ml liquid bacterial culture and illustrate the increased antagonistic effect of MV preparations from DSM 17938 on TrpV1 in response to an inducing biotic treatment.

Example 11—Alterations in Immune Modulation as a Result of Biotic Treatments During Cultivation In this Example, it has been shown that MVs derived from the cell free supernatant (CFS) of *Lactobacillus reuteri* DSM 32846 has stronger immune modulatory effect (increase in IL-6) compared to MVs derived from the cell free supernatant (CFS) of *Lactobacillus reuteri* DSM 17938. It has also been shown that the immune modulatory effect of the MVs derived from the cell free supernatant (CFS) from either *Lactobacillus reuteri* DSM 32846 or *Lactobacillus reuteri* DSM 17938 is improved after a biotic treatment during cultivation.

Material and Methods

Ethical Statement and Isolation of Peripheral Blood Mononuclear Cells

Healthy, anonymous, adult volunteers (age 18-65) were included in this study, which was approved by the Regional Ethics Committee at the Karolinska Institute, Stockholm, Sweden {Dnr 04-106/1 and 2014/2052-32}. All study subjects gave their informed written consent. Venous blood was collected in heparinized vacutainer tubes (BD Biosciences Pharmingen) and diluted with RPMI-1640 cell culture medium supplemented with 20 mM HEPES (HyClone Laboratories, Inc.). Peripheral blood mononuclear cells (PBMC) were then isolated by Ficoll-Hypaque (GE Healthcare Bio-Sciences AB) gradient separation. The PBMC were washed in RPMI-1640, resuspended in freezing medium containing RPMI-1640 40%, fetal calf serum 50% and DMSO 10%, gradually frozen in a freezing container (Mr Frosty, Nalgene Cryo 1° C.; Nalge Co.) and stored in liquid nitrogen.

In Vitro Stimulation of PBMC

PBMC were thawed, washed and viability assessed by Trypan blue staining followed by counting with a 40× light microscope. Cells were re-suspended in cell culture medium (RPMI-1640 supplemented with HEPES (20 mM), penicillin (100 U/ml), streptomycin (100 µg/ml), L-glutamine (2 mM) (all from HyClone Laboratories, Inc.) and fetal calf serum 10% (Gibco by Life Technologies)) at a final concentration of $1 \times 10^6$ cells/ml. Cells were seeded in flat-bottomed cell culture plates and incubated at 37° C. with 5% $CO_2$ atmosphere. Isolated MVs from the different bacterial preparations as described in more detail below were added to PBMC at a MV-to-cell ratio of 500:1.

Isolation of Microvesicles

*Lactobacillus reuteri* DSM 17938 or DSM 32846 bacterial cells were grown in SIM (simulated intestinal media, recipe described in Example 1) for 48 h at 37° C. For the experiments in which different biotic treatments were investigated, *Lactobacillus reuteri* DSM 17938 or DSM 32846 bacterial cells were grown in the presence of supernatants from separately grown *Bifidobacterium longum* DSM 32947 or *Bifidobacterium longum* ATCC BAA-999 in SIM for 48 h at 37° C. Also *Lactobacillus reuteri* DSM 17938 bacterial cells were grown in the presence of 25% bacterial cells from *Bifidobacterium longum* DSM 32947.

The bacterial cells were removed from the culture broth by centrifugation at 5,000×g for 10 min at 4° C. and followed by another centrifugation at 10,000×g for 10 min at 4° C. Then, the supernatants were filtrated using 0.45 µm pore filter (Millipore). Cell free supernatants were concentrated using Amicon Ultra filter unit with a MwCO of 100 kDa, which remove proteins and other molecules under 100 kDa. The supernatants were centrifuged by Beckman coulter Optima L-80XP. ultracentrifuge (Beckman coulter, United States) at 118,000×g at 4° C. for 3 h. The supernatants were discarded, resuspended the pellet in PBS buffer and ultra-centrifuged for the second time (118,000×g at 4° C. for 3 h). The pellets were then dissolved in Neurobasal A+supplement B27+Glutamax, aliquoted and stored at −70° C.

Experimental Procedure

The isolated MVs from the different bacterial preparations described above were added to PBMC at a MV-to-cell ratio of 500:1 and incubated for 48 h. The cell culture supernatants were collected and analyzed for induction of cytokines using ELISA.

ELISA

Secreted levels of the cytokine IL-6 was measured in cell culture supernatants using sandwich ELISA kits according to the manufacturer's instructions (MabTech AB). Absorbance was measured at a wavelength of 405 nm using a micro-plate reader (Molecular Devices Corp.) and results analyzed using SoftMax Pro 5.2 rev C (Molecular Devices Corp.).

Results

Figures 17, 18:
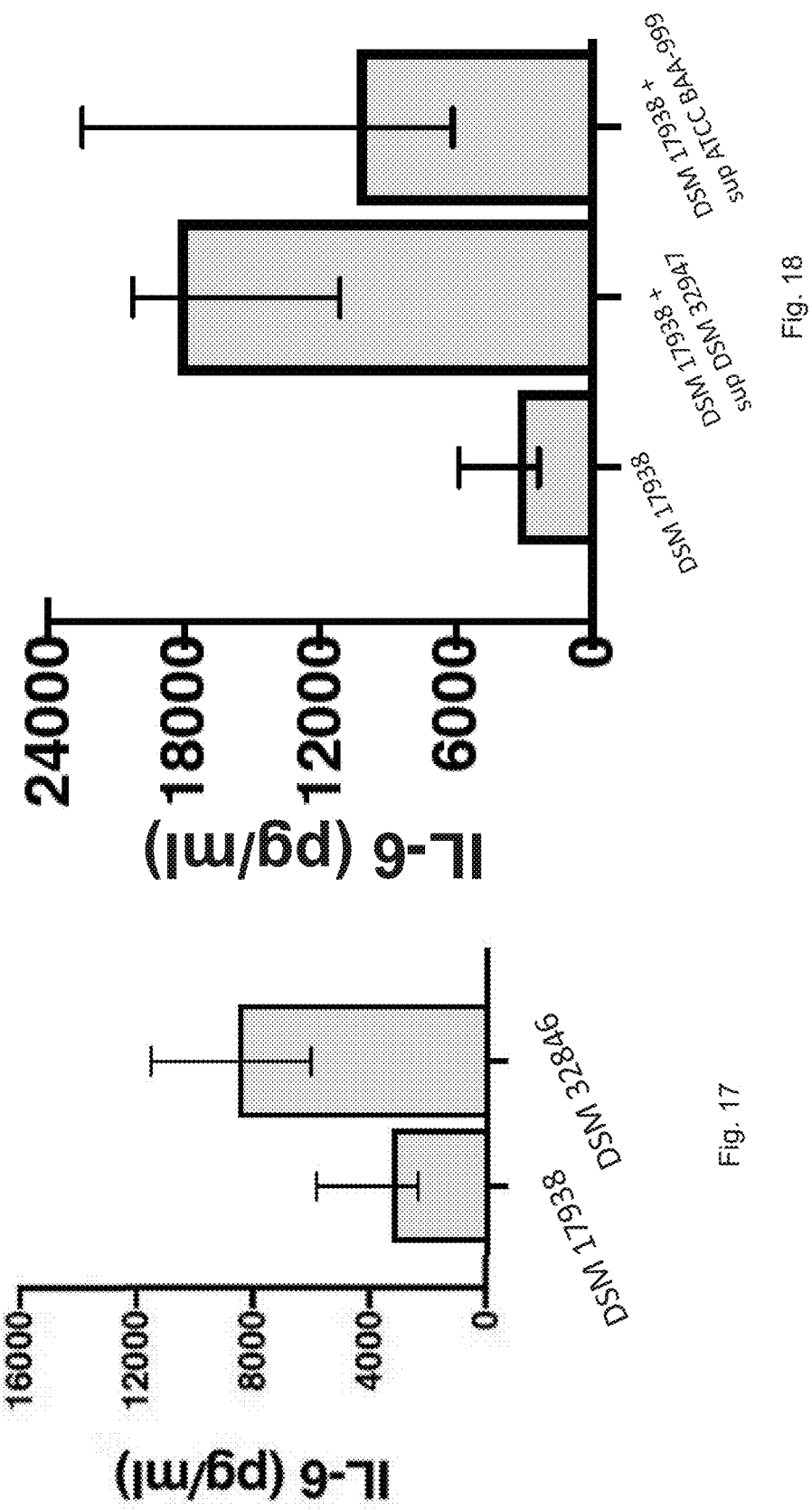
FIG. 17 illustrates that microvesicles derived from *L. reuteri* DSM 32846 are more effective in inducing the production of IL-6 compared to microvesicles isolated from *L. reuteri* DSM 17938.
FIGS. 18 and 19 illustrates the induction of IL-6 by MVs isolated from *L. reuteri* DSM 32846 and *L. reuteri* DSM 17938 after culturing with a 4% supernatant from strains of *B. longum* as compared to control samples (DSM 32846 or DSM 17938 respectively).
Figure 19:
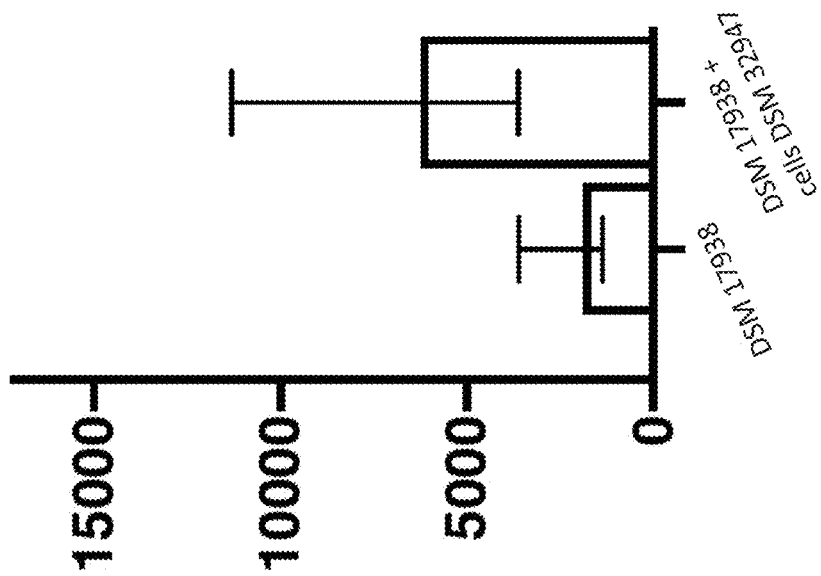
Figure 20:
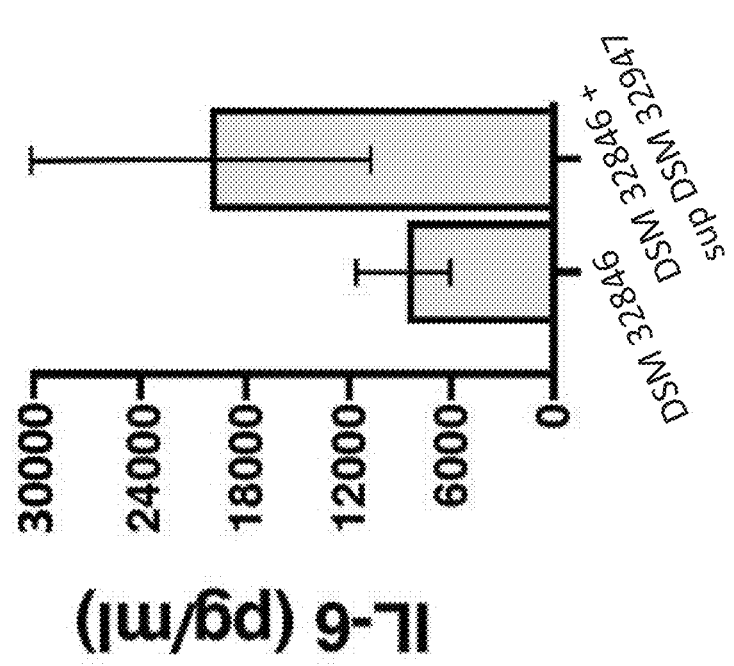
FIG. 20 illustrates the induced production of IL-6 with *L. reuteri* DSM 17938 derived MVs after co-culture with 25% cells from the *B. longum* DSM32947 as compared to control samples (DSM 17938).

Microvesicles from *Lactobacillus reuteri* DSM 32846 were more effective in inducing the production of IL-6 compared to microvesicles isolated from *Lactobacillus reuteri* DSM 17938 (FIG. 17). Moreover, MVs isolated from both strains of *Lactobacillus reuteri* after co-culturing with a *Bifidobacterium longum* strain (both 4% supernatant and 25% cells) increased the induced production of IL-6 as compared to controls (FIGS. 18, 19 and 20). These results show that isolated MVs are more effective after a biotic treatment during culturing.

Example 12 —*Lactobacillus reuteri* Derived Microvesicles (MVs) Protect Epithelial Barrier Integrity from the Detrimental Effect of Enterotoxigenic *Escherichia coli*

Material and Methods

Isolation of Extracellular Microvesicles (MVs)

*Lactobacillus reuteri* DSM 17938 or *Lactobacillus reuteri* DSM 32846 bacterial cells were grown in Man-Rogosa-Sharpe medium, harvested after 24 h and removed from the culture broth by centrifuging at 5,000×g for 10 min at 4° C. and followed by centrifugation at 10,000×g for 10 min at 4° C., after which any residual cells were removed from the supernatant by filtration using 0.45 µm pore filter. Supernatants were concentrated using Amicon Ultra filter (100 kDa), which remove proteins and other molecules under 100 kDa. The supernatants were centrifuged by Beckman coulter Optima L-80XP ultracentrifuge (Beckman coulter, United States) at 118,000×g at 4° C. for 3 h. The supernatants were discarded, the pellets were resuspended in PBS buffer and ultra-centrifuged for the second time (118,000×g at 4° C. for 3 h). The pellets were then dissolved in PBS, aliquot and stored at −70° C.

Intestinal Permeability In Vitro (Caco-2/HT29 Cell Co-Cultures)

Epithelial Cell Culture (Caco-2/HT29)

Caco-2 and HT29 epithelial cells were separately grown in tissue culture flasks in Dulbecco's Modified Eagle's Medium (DMEM) supplemented with 10% fetal bovine serum, 1% non-essential amino acids, and 1% penicillin and streptomycin, at 37° C. under an atmosphere of 5% $CO_2$ with 90% relative humidity. Caco-2 and HT29 cells were grown in 25 $cm^2$ tissue culture flasks and split at 80-90% confluence using 0.25% trypsin and 0.02% ethylenediaminetetraacetic acid (EDTA) solution. The cells were seeded at a density of $6 \times 10^4$ cells per 25-$cm^2$ flask.

Cell Co-Cultures

Caco-2 and HT29 cells were seeded on the apical chamber of Transwell inserts (Transwell-COL collagen-coated membrane filters) with 9:1 proportion and grown in 12-well Transwell plates with a final density of $1 \times 10^5$ cells/$cm^2$ in each insert. Cells were maintained in the same conditions and allowed to grow for 21 days with medium (0.5 ml in the apical side and 1.5 ml in the basolateral side) changes every other day to allow the cells to become differentiated.

Cell Layer Integrity

The integrity of the cell layer was determined using two methods: Transepithelial electrical resistance (TEER) and determination of fluorescein isothiocyanate-dextran (FITC-dextran) permeability.

The cell monolayer integrity during the experiments was determined by Transepithelial electrical resistance (TEER) measurement using the Millicell electrical resistance system (Millipore, Darmstadt, Germany). Three different areas were chosen to detect the TEER values in each well and the averages were the final results. TEER values above 250 $\Omega cm^2$ were used for the permeability studies.

Seeded Caco-2/HT29 cells were pre-treated with either live *Lactobacillus reuteri* DSM 17938 or *Lactobacillus reuteri* DSM 32846 cells at 100 multiplicity of bacteria (MOB) or extracellular microvesicles (MVs) from *Lactobacillus reuteri* DSM 17938 or *Lactobacillus reuteri* DSM 32846 cells at 200 multiplicity of MV (MOM) for 6 h before challenge with ETEC (pathogenic enterotoxigenic *E. coli*, known for having a disruptive effect on epithelial integrity) at 100 multiplicity of infection (MOI) for an additional 6 h. TEER was measured prior to pre-treatment and challenge with ETEC, followed by measurement every second hour during the entire challenge. In order to quantify the paracellular permeability of monolayers, 1 mg/mL of 4 kDa fluorescein isothiocyanate-dextran (FITC-dextran; Sigma) was added to the apical side of the inserts at the start of the challenge with ETEC. Samples from the basolateral compartment were taken after 6 h of incubation. The diffused fluorescent tracer was then analyzed in triplicate by fluorometry (excitation, 485 nm; emission, 520 nm) using a FLUOstar Omega Microplate Reader (BMG Labtech, Ortenberg, Germany).

Results

Figure 21:
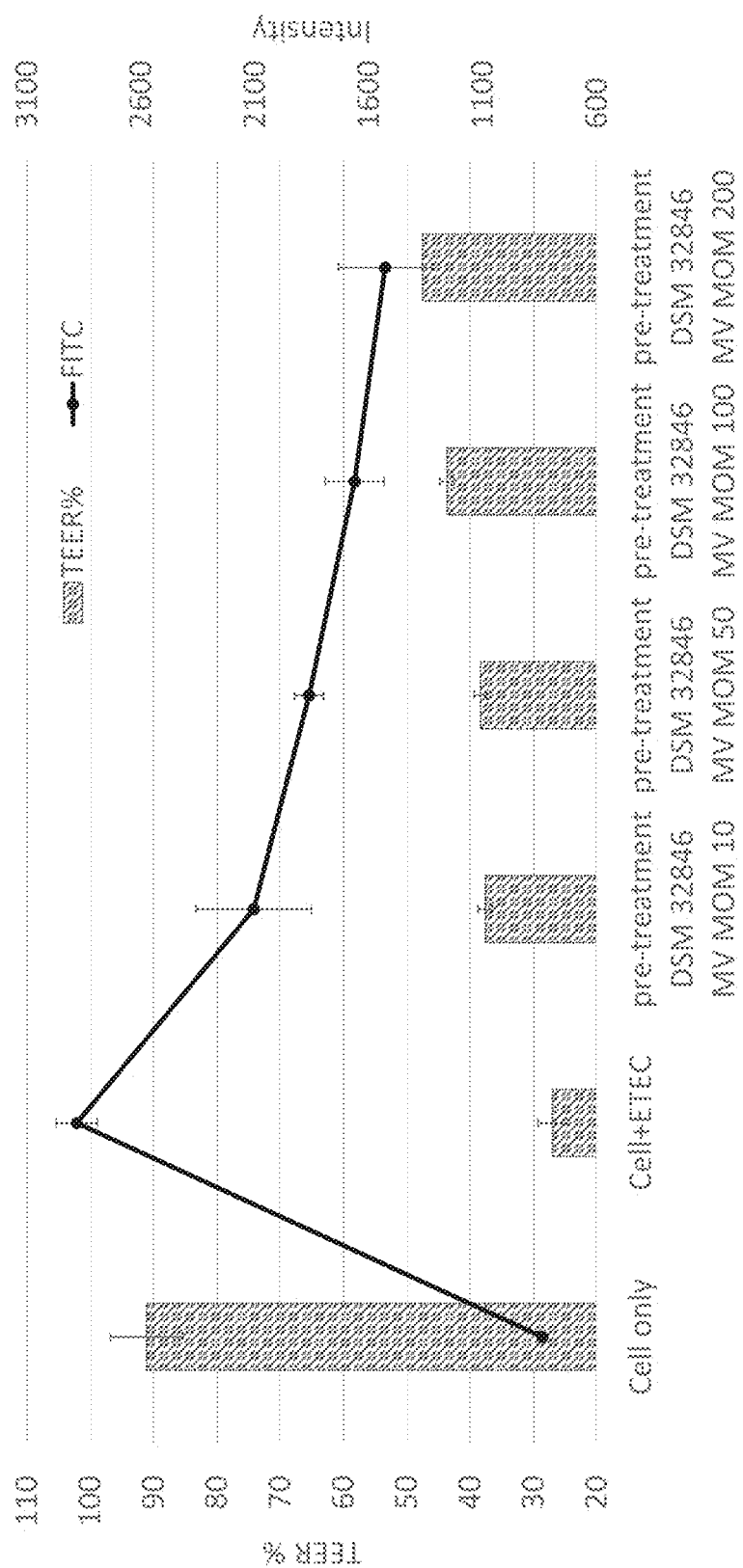
FIG. 21 illustrates that *L. reuteri* DSM 32846 derived MVs were partly able to protect the epithelial monolayer from a challenge with ETEC induced reduction in TEER.

The challenge with ETEC induced a reduction in TEER illustrating that *L. reuteri* DSM 32846 derived MVs were partly able to protect the epithelial monolayer from this challenge (FIG. 21). At 6 h after ETEC challenge, the decline of TEER for the ETEC group reached 27% whereas pre-treatment with the *L. reuteri* DSM 32846 derived MVs of 10, 50, 100, and 200 MOM showed considerably higher TEER as compared to the ETEC treated group. Untreated cells remained at around 90%.

This protective effect of *L. reuteri* DSM 32846 derived MVs against ETEC damage to the monolayer was also apparent in the FITC-dextran flux experiments (FIG. 21). Pre-treatment of the monolayers with *L. reuteri* DSM 32846 derived MVs of 10, 50, 100, and 200 MOM decreased the leakage of FITC-dextran compared with the ETEC group.

Thus, *L. reuteri* DSM 32846 derived MVs showed protection effect of the ETEC-induced damage to the Caco-2/HT29 co-cultures monolayers.

In FIG. 22, a comparison between the protective effect of *L. reuteri* DSM 32846 derived MVs as shown in the FITC-dextran flux experiment was compared to the effect obtained with *L. reuteri* DSM 17938 derived MVs. Pre-treatment of the epithelial cell monolayers with *L. reuteri* DSM 32846 derived MVs decreased the leakage of FITC-dextran more efficiently, specifically at lower concentrations of MVs, compared to *L. reuteri* DSM 17938 derived MVs. This shows that *L. reuteri* DSM 32846 derived MVs are more efficient than *L. reuteri* DSM 17938 derived MVs in protecting epithelial barrier integrity.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Abusleme, L. et al. IL-17; overview and role in oral immunity and microbiome. *Oral Dis.* 23(7): 854-865 (2017).
Bindels, L. et al. Increased gut permeability in cancer cachexia: mechanisms and clinical relevance. *Oncoraget.* Vol. 9, (No. 26), pp:18224-18238, (2018).
DiRienzo, J. Breaking the Gingival Epithelial Barrier: Role of the *Aggregatibacter actinomycetemcomitans* Cytolethal Distending Toxin in Oral Infectious Disease. Cells. 3, 476-499, (2014).
Funauchi, M. et al. Serum level of interferon-gamma in autoimmune diseases, *Tohoku J Exp Med.* 164(4): 259-267 (1991).
Gu, Z. W. et al. Neutralization of interleukion-17 suppresses allergic rhinitis symptoms by downregulating Th2 and Th17 responses and upregulating the Treg response. *Oncoraget.* Vol. 8, (No. 14), pp:22361-22369, (2017).
Heitler, W. J. DataView: A Tutorial Tool for Data Analysis. Template-based Spike Sorting and Frequency Analysis. *J. Undergrad. Neurosci. Educ.* 6, A1-7 (2007).
Klonowska, J. et al. New Cytokines in the Pathogenesis of Atopic Dermatitis—New Therapeutic Targets. *Int. J. Mol Sci.* 19, 3086 (2018).
Koga, C. et al. Possible Pathogenic Role of Th17 Cells for Atopic Dermatitis. *Journal of Investigative Dermatology.* 128, 2625-2630, (2008).
Lee, Youngkyun. The role of interleukin-17 in bone metabolism and inflammatory skeletal diseases. *BMB Reports.* 46 (1): 479-483 (2013).
Perez-Burgos, A. et al. Psychoactive bacteria *Lactobacillus rhamnosus* (JB-1) elicits rapid frequency facilitation in vagal afferents. *Am. J. Physiol. Gastrointest. Liver Physiol.* 304, G211-G220 (2013).
Perez-Burgos, A. et al. Transient receptor potential vanilloid 1 channel in rodents is a major target for antinociceptive effect of the probiotic *L. reuteri* DSM 17938. *J. Physiol.* 17, n/a-n/a (2015).
Pollard, K. M et al. Interferon-γ and systemic autoimmunity, *Discov. Med.* 16(87), 123-131 (2013).
Tachibana, K. et al. IL-17 and VEGF are increased and correlated to systemic inflammation, immune suppression, and malnutrition in patients with breast cancer. *International Journal of Immunopathology and Pharmacology. Vol.* 15(3) 219-228, (2017).
Wang, Y-H. et al. The cytokine family and their role in allergic inflammation. *Curr Opin Immunol.* 20(6): 697-702, (2008).
Wu, R. Y. et al. Spatiotemporal maps reveal regional differences in the effects on gut motility for *Lactobacillus reuteri* and *rhamnosus* strains. *Neurogastroenterol. Motil.* 25, e205-e214 (2013).
Zbikowska-Gotz, M. et al. Expression of IL17A concentration and effector functions of peripheral blood neutrophils in food allergy hypersensitivity patients. International Journal of Immunopathology and Pharmacology. Vol. 29(1) 90-98, (2015).
Zhang, J. et al. Changes of serum cytokines-related Th1/Th2/Th17 concentration in patients with postmenopausal osteoporosis. *Gynecological Endrocrinology,* 31:3, 183-190 (2015).

The invention claimed is:

1. An isolated bacterial strain, wherein the bacterial strain is *Bifidobacterium longum* DSM 32947 or *Bifidobacterium longum* DSM 32948, wherein the bacterial strain is dried or lyophilized.

2. A composition comprising bacteria of at least one isolated bacterial strain of claim 1, wherein the bacteria are capable of inducing production of therapeutic microvesicles by another bacteria.

3. The composition of claim 2, wherein the bacterial strain is *Bifidobacterium longum* DSM 32947, and wherein the bacterial strain is spray-dried, spray-freeze dried, or vacuum-dried.

4. The composition of claim 2, wherein the bacterial strain is *Bifidobacterium longum* DSM 32948, and wherein the bacterial strain is spray-dried, spray-freeze dried, or vacuum-dried.

5. The isolated bacterial strain of claim 1, wherein the bacterial strain is *Bifidobacterium longum* DSM 32947.

6. The isolated bacterial strain of claim 1, wherein the bacterial strain is *Bifidobacterium longum* DSM 32948.

7. A probiotic composition comprising bacteria of at least one isolated bacterial strain of claim 1 and bacteria of a *Lactobacillus reuteri* strain selected from *L. reuteri* DSM 17938, *L. reuteri* DSM 32846, and a combination thereof.

8. The probiotic composition of claim 7, wherein the bacterial strain is *Bifidobacterium longum* DSM 32947, and wherein the *Lactobacillus reuteri* strain is *L. reuteri* DSM 17938.

9. The probiotic composition of claim 7, wherein the bacterial strain is *Bifidobacterium longum* DSM 32947, and wherein the *Lactobacillus reuteri* strain is *L. reuteri* DSM 32846.

10. The probiotic composition of claim 7, wherein the bacterial strain is *Bifidobacterium longum* DSM 32947, and wherein the *Lactobacillus reuteri* strain is a combination of *L. reuteri* DSM 17938 and *L. reuteri* DSM 32846.

11. The probiotic composition of claim 7, wherein the bacterial strain is *Bifidobacterium longum* DSM 32948, and wherein the *Lactobacillus reuteri* strain is *L. reuteri* DSM 17938.

12. The probiotic composition of claim 7, wherein the bacterial strain is *Bifidobacterium longum* DSM 32948, and wherein the *Lactobacillus reuteri* strain is *L. reuteri* DSM 32846.

13. The probiotic composition of claim 7, wherein the bacterial strain is *Bifidobacterium longum* DSM 32948, and wherein the *Lactobacillus reuteri* strain is a combination of *L. reuteri* DSM 17938 and *L. reuteri* DSM 32846.

* * * * *